(12) United States Patent
Keith et al.

(10) Patent No.: US 6,489,481 B1
(45) Date of Patent: Dec. 3, 2002

(54) METHOD FOR TREATING NEUROLOGICAL DISORDERS

(75) Inventors: Richard Alan Keith, Wilmington, DE (US); Timothy Martin Piser, Wilmington, DE (US); Michael Thaddeus Klimas, Waukesha, WI (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/831,211

(22) PCT Filed: Oct. 29, 1999

(86) PCT No.: PCT/GB99/03583

§ 371 (c)(1),
(2), (4) Date: Jun. 25, 2001

(87) PCT Pub. No.: WO00/25767

PCT Pub. Date: May 11, 2000

(30) Foreign Application Priority Data

Nov. 4, 1998 (GB) .............................................. 9824207

(51) Int. Cl.$^7$ .............................................. C07D 211/18
(52) U.S. Cl. ........................... 546/232; 549/12; 560/37; 564/305
(58) Field of Search ............................. 514/239.2, 317, 514/428, 648; 546/232; 549/12; 560/37; 564/305

(56) References Cited

FOREIGN PATENT DOCUMENTS

| EP | 792638 A1 | * 9/1997 |
| WO | WO 96/40098 | * 12/1996 |

* cited by examiner

*Primary Examiner*—Zinna Northington Davis

(57) ABSTRACT

Treatment or the prevention of neurological disorders in a warm-blooded mammal, by use of a compound of formula VIII

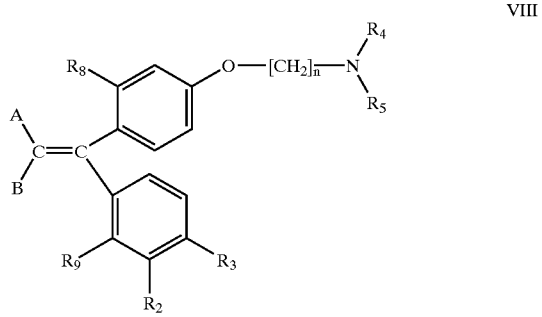

wherein A, B, $R_2$, $R_3$, $R_4$, $R_5$, $R_8$, $R_9$ and n are as defined in the specification, or pharmaceutically-acceptable salts, prodrugs or solvates thereof. Processes for the preparation of compounds of Formula VIII are described, as are pharmaceutical compositions containing them.

1 Claim, No Drawings

METHOD FOR TREATING NEUROLOGICAL DISORDERS

CROSS REFERENCE TO RELATED APPLICATIONS

This is a National Phase Application of International Application PCT/GB99/03583, filed Oct. 29, 1999, which claims priority from U.K. Application No. 9824207.6, filed Nov. 4, 1998.

This invention relates to methods of preventing and treating neurological disorders such as cognitive disorders, and/or neurological disorders related to neuronal apoptosis and/or excitotoxicity, for example Alzheimer's disease, vascular dementia and age-related dementia as well as head trauma, stroke, spinal cord injury, amyotrophic lateral sclerosis (ALS), Parkinson's disease, Huntington's chorea, AIDS-related dementia, peripheral neuropathies and macular degeneration. Such methods comprise the administration to a warm-blooded mammal, such as a human, in need thereof an effective amount of a compound of Formula I or Formula VIII. This invention also relates to the use of a compound of Formula I or Formula VIII for the manufacture of a medicament for the prevention or treatment of the aforementioned disorders.

BACKGROUND TO THE INVENTION

Alzheimer's Disease (AD) is the most common form of dementia, affecting approximately 4 million people in the United States alone. AD is a degenerative brain disorder characterized clinically by progressive loss of memory, cognition, reasoning, judgment and emotional stability that gradually leads to profound mental deterioration and ultimately death. AD is a common cause of progressive mental failure (dementia) in aged humans and is believed to represent the fourth most common medical cause of death in the United States. AD has been observed in varied races and ethnic groups worldwide and presents a major present and future public health problem. To date, AD has proven to be incurable. For recent reviews of Alzheimer's disease see: Edelberg & Wei (1996) Mech Aging & Development 91: 95 and De LaTorre (1994) Neurosci & Biobehavioral Reviews 18:397.

The brains of individuals with AD exhibit neuronal degeneration and characteristic lesions variously referred to as amyloidogenic plaques, vascular amyloid angiopathy, and neurofibrillary tangles. Large numbers of these lesions, particularly amyloidogenic plaques and neurofibrillary tangles, are generally found in several areas of the human brain important for memory and cognitive function in patients with AD. Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome) and Hereditary Cerebral Hemorrhage with Amyloidosis of the Dutch-Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

Several lines of evidence indicate that progressive cerebral deposition of particular amyloidogenic proteins, b-amyloid proteins, (b-AP), play a seminal role in the pathogenesis of AD and can precede cognitive symptoms by years or decades. See, Selkoe, (1991) Neuron 6:487. It has been shown that b-AP is released from neuronal cells grown in culture and is present in cerebrospinal fluid (CSF) of both normal individuals and AD patients. See, Seubert et al., (1992) Nature 359:325–327.

A growing amount of research suggests that the pathogenesis of AD is due to impaired vascular delivery of nutrients to the brain. It is suggested that abnormal haemodynamic flow patterns caused by structural deformities of the capillaries leads to dysfunctional cerebral transport of nutrients. The production of plaques and neurofibrillary tangles may develop from hypometabolic abnormalities caused by the impaired cerebromicrovasculature (for a review see: de la Torre (1997) Gerontology 43:26).

Vascular dementia is considered to be the second most common cause of dementia in Europe and the US. In Asia and many developing countries, it is more common than dementia of the Alzheimer's type. Vascular dementia describes global cognitive decline attributed to the cumulative effects of ischemic vascular disease. Discrete and multiple cognitive skills, including memory, are successively lost as a result of focal cerebrovascular insults. (For a recent review of vascular dementia see: Konno et al (1997) Drugs and Aging, 11:361).

DESCRIPTION

Emopamil is a neuroprotective agent structurally related to the $Ca^{2+}$ antagonist, verapamil. However, verapamil is only a weak $Ca^{2+}$ inhibitor in the brain due to limited CNS access. Emopamil, but not verapamil, binds a high affinity site which is present in the endoplasmic reticulum in a number of tissues including brain and liver. Recently, it has been suggested that the emopamil binding protein (EBP) represents an anti-ischemic binding site (Moebius et al, (1993) Mol Pharmacol 43:139). More recently Silve et al have shown that the EBP exhibits $\Delta 8$-$\Delta 7$ sterol isomerase activity when expressed in yeast (Silve et al (1996) J.Biol. Chem.271:22434). $\Delta 8$-$\Delta 7$ sterol isomerase is a post squalene enzyme which participates in the conversion of lanosterol to cholesterol.

Surprisingly we have found that the a compound of formula I or formula VIII binds with high affinity to EBP and that a compound of formula I or formula VIII inhibits neuronal cell death in a number of assays of neurodegeneration. The present invention is also based on surprising discovery that a compound of formula I or formula VIII inhibits neuronal apoptosis and excitotoxicity, mechanistically two distinct pathways to neuronal death, and that therefore the compounds of the invention described herein and the pharmaceutically acceptable salts, prodrugs and solvates thereof may be of value in the treatment and/or prevention of neuronal apoptosis and/or excitotoxicity related neurological disorders.

Thus according to the present invention there is provided a method of treating or preventing cognitive disorders, such as Alzheimer's disease, vascular dementia and age-related dementia, in a warm-blooded mammal, such as man, which comprises administering an effective amount of a compound of Formula I:

Formula I

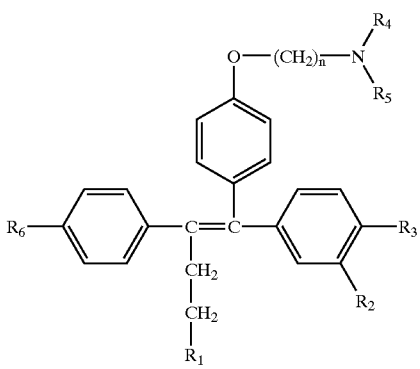

(where $R_1$ is hydrogen or halo; $R_2$ is hydrogen or hydroxy; $R_3$ is hydrogen, hydroxy, halo or $PO_4$; $R_4$ and $R_5$ are either both methyl, are both ethyl or together with the nitrogen atom to which they are attached form a ring selected from pyrrolidine, piperidine or morpholine; $R_6$ is hydrogen or a $C_{1-4}$ straight or branched alkyl chain and n is 2 or 3) or a pharmaceutically acceptable salt, prodrug or solvate thereof.

Convenient values for $R_1$ are hydrogen or halo, preferably hydrogen or chloro, most preferably hydrogen.

Convenient values for $R_2$ are hydrogen or hydroxy, preferably hydrogen;

Convenient values for $R_3$ are hydrogen, hydroxy, halo or $PO_4$, preferably hydrogen, hydroxy, iodo or $PO_4$, most preferably hydrogen.

Convenient values for $R_4$ and $R_5$ are either both methyl or both ethyl or $R_4$ and $R_5$ together with the nitrogen atom to which they are attached form a ring selected from pyrrolidine, piperidine or morpholine, preferably $R_4$ and $R_5$ are both methyl or together with the nitrogen to which they are attached form a pyrrolidine ring; most preferably $R_4$ and $R_5$ are both methyl.

Convenient values for $R_6$ are hydrogen or a straight or branched $C_{1-4}$ alkyl chain, preferably hydrogen or isopropyl, most preferably hydrogen.

Convenient values for n are 2 or 3, preferably 2.

According to a further aspect of the present invention there is provided a method of treating or preventing neurological disorders, in a warm-blooded mammal, such as man, which comprises administering an effective amount of a compound of Formula VIII.

Formula VIII

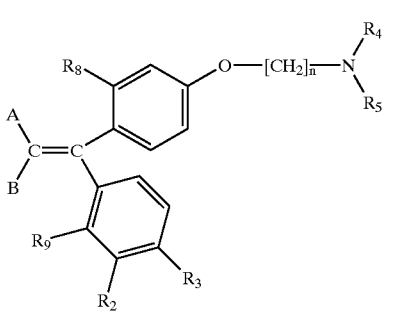

wherein

A and B are selected from:

Formula IX

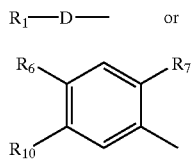

Formula X such that when A is of Formula X then B is of Formula IX and when A is of Formula IX then B is of Formula X.

$R_1$ is selected from hydrogen, halo, aryl, carbamoyl, N—$C_{1-4}$alkylcarbamoyl or NN—di—$C_{1-4}$alkylcarbamoyl;

D is selected from $C_{1-4}$alkylene, $C_{1-4}$alkenylene or $C_{1-4}$alkynylene;

$R_2$ is selected from hydrogen, $C_{1-4}$alkyl or hydroxy;

$R_3$ is selected from hydrogen, hydroxy, halo, $PO_4$, $C_{1-4}$alkoxy, or a group of the formula:

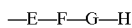

wherein:
E is selected from

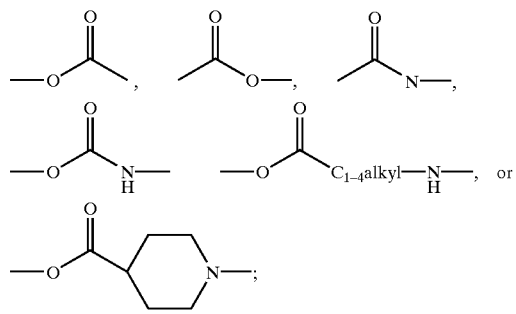

F is selected from

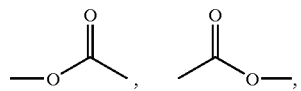

or a direct bond;

G is selected from $C_{1-6}$alkylene, or a direct bond;

H is selected from hydrogen, $C_{1-4}$alkoxy, aryl; heteroaryl, carbocyclyl, wherein the aryl, heteroaryl or carbocyclyl may be optionally substituted (on an available carbon atom) by up to 3 substituents independently selected from halo, $C_{1-4}$alkyl, $C_{1-4}$alkoxy, halo, amino, N—$C_{1-4}$alkylamino, NN—di—$C_{1-4}$alkylamino, amino$C_{1-4}$alkyl, or aryl;

$R_4$ and $R_5$ are independently selected from $C_{1-4}$alkyl, or together with the nitrogen atom to which they are attached form a ring selected from pyrrolidine, piperidine or morpholine;

$R_6$ is selected from hydrogen, $C_{1-4}$alkyl; $C_{1-4}$alkoxy, halo, or a ring fused phenyl group fused via carbons 3 and 4 on the phenyl group of formula X;

$R_7$ and $R_8$ are either both hydrogen or when A is of Formula X may be joined either via a sulphur atom, via —$CH_2$— or via —$CH_2CH_2$— to form a seven membered sulphur-containing ring, a seven-membered ring or an eight membered ring respectively;

$R_9$ is selected from hydrogen or $C_{1-4}$alkyl;

$R_{10}$ is selected from hydrogen, $C_{1-4}$alkyl or halo; and n is 2 or 3;

or a pharmaceutically acceptable salt, prodrug or solvate thereof.

Compounds used in the methods of the invention can exist in both the cis and trans configuration. Both these configurations are active in the biochemical and cellular assays described below. This is reflected in the values for A and B in Formula VIII.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

The term "aryl" refers to phenyl or naphthyl.

The term "heteroaryl" refers to a 5–10 membered aromatic mono or bicyclic ring containing up to 5 heteroatoms independently selected from nitrogen, oxygen or sulphur, linked via ring carbon atoms or ring nitrogen atoms where a bond from a nitrogen is allowed, for example no bond is possible to the nitrogen of a pyridine ring, but a bond is possible through the 1-nitrogen of a pyrazole ring. Examples of 5- or 6-membered heteroaryl ring systems include pyrrole, furan, imidazole, triazole, pyrazine, pyrimidine, pyridazine, pyridine, isoxazole, oxazole, 1,2,4 oxadiazole, isothiazole, thiazole and thiophene. A 9 or 10 membered bicyclic heteroaryl ring system is an aromatic bicyclic ring system comprising a 6-membered ring fused to either a 5 membered ring or another 6 membered ring. Examples of 5/6 and 6/6 bicyclic ring systems include benzofuran, benzimidazole, benzthiophene, benzthiazole, benzisothiazole, benzoxazole, benzisoxazole, indole, pyridoimidazole, pyrimidoimidazole, quinoline, isoquinoline, quinoxaline, quinazoline, phthalazine, cinnoline and naphthyridine.

The term "heterocyclyl" refers to a 5–10 membered saturated or partially saturated mono or bicyclic ring containing up to 5 heteroatoms selected from nitrogen, oxygen or sulphur linked via ring carbon atoms or ring nitrogen atoms. Examples of 'heterocyclyl' include pyrrolinyl, pyrrolidinyl, morpholinyl, piperidinyl, piperazinyl, dihydropyridinyl and dihydropyrimidinyl The term "carbocyclyl" refers to a totally saturated or partially saturated mono, bi or tri cyclic carbon ring. Examples of carbocyclic rings are cyclopentyl, cyclohexyl, bicyclo-octane or adamantyl.

The term "halo" refers to fluoro, chloro, bromo or iodo.

The term carbamoyl refers to —C(O)NH$_2$.

Examples of $(C_{1-4})$alkyl include methyl, ethyl, propyl, isopropyl, sec-butyl and tert-butyl; examples of $(C_{1-4})$ alkoxy include methoxy, ethoxy and propoxy; examples of N—$(C_{1-4})$alkylcarbamoyl include methylaminocarbonyl, ethylaminocarbonyl, propylaminocarbonyl, isopropylaminocarbonyl, sec-butylaminocarbonyl and tert-butylaminocarbonyl; examples of NN-di-$(C_{1-4}$alkyl) carbamoyl include di-methylaminocarbonyl, di-ethylaminocarbonyl and N-ethyl-N-methylaminocarbonyl; Examples of $(C_{1-4})$alkenylene include propenylene and 2-butenylene, or

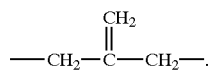

Examples of $(C_{1-4})$alkynylene include:

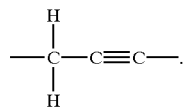

Convenient values for $R_1$ are hydrogen, halo, phenyl or NN-di-$C_{1-4}$alkylcarbamoyl. Preferably hydrogen, chloro, NN-di-ethylcarbamoyl. Most preferably hydrogen.

Convenient values for D are methylene, ethylene, propylene, ethenylene or propenylene. Preferably 2-propenylene or ethylene. Most preferably 2-propenylene.

Convenient values for $R_2$ are hydrogen or $C_{1-4}$alkyl; Preferably methyl, ethyl or hydrogen. Most preferably hydrogen.

Convenient values for $R_3$ are hydrogen hydroxy, $C_{1-4}$alkoxy, or a group of the formula: —E—F—G—H. Preferably hydrogen, hydroxy, methoxy, or a group of the formula:—E—F—G—H. Most preferably hydrogen, hydroxy or methoxy.

Convenient values for E

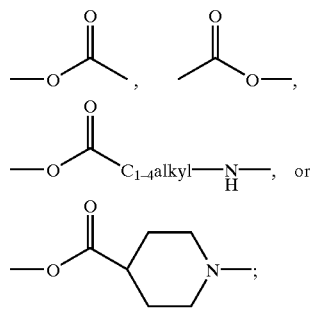

Preferably

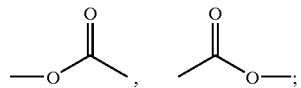

Most preferably

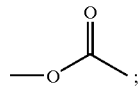

Convenient values for F are

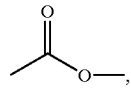

or a direct bond;

Preferably a direct bond.

Convenient values for G are ethylene, methylene, propylene, 1,1-dimethylethylene (wherein carbon 1 is attached to F) or a direct bond. Preferably methylene, 1,1-dimethylethylene or a direct bond. Most preferably 1,1-dimethylethylene or a direct bond.

Convenient values for substituents on an aryl, heteroaryl or carbocyclyl ring at H are $C_{1-4}$alkyl, halo, amino or —$C_{1-4}$alkylamino. Preferably $C_{1-4}$alkyl or amino. Most preferably amino.

Convenient values for $R_4$ and $R_5$ are either independently methyl, ethyl or phenyl, or together with the nitrogen atom to which they are attached form a ring selected from pyrrolidine, piperidine or morpholine. Preferably $R_4$ and $R_5$, each represent methyl, each represent ethyl, $R_4$ is methyl and $R_5$ is phenyl, or $R_4$ and $R_5$ together form a pyrrolidino or piperidino ring. More preferably $R_4$ and $R_5$ each represent methyl, or $R_4$ and $R_5$ together represent a pyrrolidino ring, especially $R_4$ and $R_5$ each represent methyl or together represent a pyrrolidino ring.

Convenient values for $R_6$ are $C_{1-4}$alkyl, halo. More preferably chloro, fluoro or $C_{1-4}$alkyl. Preferably chloro, fluoro or ethyl. Most preferably ethyl or fluoro.

Convenient values for $R_7$ and $R_8$ are $R_7$ and $R_8$ each represent hydrogen or $R_7$ and $R_8$ together form an eight membered carbon ring or 7-membered sulphur containing ring as above. Preferably $R_7$ and $R_8$ each represent hydrogen or $R_7$ and $R_8$ together form a 7-membered sulphur containing ring as above. Most preferably $R_7$ and $R_8$ each represent hydrogen.

Convenient values for $R_9$ are hydrogen or ethyl. Most preferably hydrogen.

Convenient values for $R_{10}$ are hydrogen, methyl, ethyl or halo. Preferably hydrogen or halo. Most preferably chloro.

A preferred group of compounds for any feature of the invention include a compound of formula VIII wherein:

$R_1$ is hydrogen; and

D is $C_{1-4}$alkenylene, preferably 2-propenylene.

A preferred group of compounds for any feature of the invention include a compound of formula VIII wherein:

$R_1$ is hydrogen;

D is $C_{1-4}$alkenylene, preferably 2-propenylene.

$R_2$ is hydrogen;

$R_3$ is hydrogen halo, hydroxy, or $C_{1-4}$alkoxy;

$R_4$ is methyl or ethyl, $R_5$ is methyl, ethyl or phenyl or together $R_4$ and $R_5$ form pyrrolidine or piperidine;

$R_6$ is hydrogen, $C_{1-4}$alkyl or halo;

$R_7$ and $R_8$ are both hydrogen; and $R_9$ is hydrogen, methyl or ethyl.

A preferred group of compounds for any feature of the invention include a compound of formula VIII wherein:

$R_1$ is hydrogen;

D is $C_{1-4}$alkenylene, preferably 2-propenylene.

$R_2$ is hydrogen;

$R_3$ is a group of the formula —E—F—G—H.

$R_4$ is methyl or ethyl, $R_5$ is methyl, ethyl or phenyl or together $R_4$ and $R_5$ form pyrrolidine or piperidine;

$R_6$ is hydrogen, $C_{1-4}$alkyl or halo;

$R_7$ and $R_8$ are both hydrogen; and $R_9$ is hydrogen, methyl or ethyl.

A preferred group of compounds for any feature of the invention include a compound of formula VIII wherein:

$R_1$ is hydrogen;

D is $C_{1-4}$alkenylene, preferably 2-propenylene.

$R_2$ is hydrogen;

$R_3$ is hydrogen halo, hydroxy, or $C_{1-4}$alkoxy;

$R_4$ is methyl or ethyl, $R_5$ is methyl, ethyl or phenyl or together $R_4$ and $R_5$ form pyrrolidine or piperidine;

$R_6$ is hydrogen, $C_{1-4}$alkyl or halo;

$R_7$ and $R_8$ are joined either via a sulphur atom, via —$CH_2$— or via —$C_2H_4$— to form a seven membered sulphur-containing ring, a seven-membered ring or an eight membered ring respectively; and $R_9$ is hydrogen, methyl or ethyl.

A preferred group of compounds for any feature of the invention include a compound of formula VIII wherein:

$R_1$ is hydrogen;

D is $C_{1-4}$alkenylene, preferably 2-propenylene.

$R_2$ is hydrogen;

$R_3$ is a group of the formula —E—F—G—H.

$R_4$ is methyl or ethyl, $R_5$ is methyl, ethyl or phenyl or together $R_4$ and $R_5$ form pyrrolidine or piperidine;

$R_6$ is hydrogen, $C_{1-4}$alkyl or halo;

$R_7$ and $R_8$ are joined either via a sulphur atom, via —$CH_2$— or via —$C_2H_4$— to form a seven membered sulphur-containing ring, a seven-membered ring or an eight membered ring respectively; and $R_9$ is hydrogen, methyl or ethyl.

A further preferred group of compounds for any feature of the invention include a compound of formula VIII wherein:

$R_1$ is hydrogen or halo or NN—$C_{1-4}$alkylcarbamoyl; and $R_4$ and $R_5$ together form pyrrolidine or piperidine.

A further preferred group of compounds for any feature of the invention include a compound of formula VIII wherein:

$R_1$ is hydrogen or halo or NN—$C_{1-4}$alkylcarbamoyl;

$R_2$ is hydrogen;

$R_3$ is hydrogen halo, hydroxy, or $C_{1-4}$alkoxy;

$R_4$ and $R_5$ together form pyrrolidine or piperidine; and $R_7$ and $R_8$ are both hydrogen.

A further preferred group of compounds for any feature of the invention include a compound of formula VIII wherein:

$R_1$ is hydrogen or halo or NN—$C_{1-4}$alkylcarbamoyl;

$R_2$ is hydrogen;

$R_3$ is a group of the formula —E—F—G—H;

$R_4$ and $R_5$ together form pyrrolidine or piperidine; and $R_7$ and $R_8$ are both hydrogen A further preferred group of compounds for any feature of the invention include a compound of formula VIII wherein:

$R_1$ is hydrogen or halo or NN—$C_{1-4}$alkylcarbamoyl;

$R_2$ is hydrogen;

$R_3$ is hydrogen halo, hydroxy, or $C_{1-4}$alkoxy;

$R_4$ and $R_5$ together form pyrrolidine or piperidine; and $R_7$ and $R_8$ are joined either via a sulphur atom, via —$CH_2$— or via —$C_2H_4$— to form a seven membered sulphur-containing ring, a seven-membered ring or an eight membered ring respectively A further preferred group of compounds for any feature of the invention include a compound of formula VIII wherein:

$R_1$ is hydrogen or halo or NN—$C_{1-4}$alkylcarbamoyl;

$R_2$ is hydrogen;

$R_3$ is a group of the formula —E—F—G—H;

$R_4$ and $R_5$ together form pyrrolidine or piperidine; and $R_7$ and $R_8$ are joined either via a sulphur atom, via —$CH_2$— or via —$C_2H_4$— to form a seven membered sulphur-containing ring, a seven-membered ring or an eight membered ring respectively.

A further preferred group of compounds for any feature of the invention include a compound of formula VIII wherein:

R₃ is hydroxy.

A further preferred group of compounds for any feature of the invention include a compound of formula VIII wherein:
$R_1$ is hydrogen or halo or NN—$C_{1-4}$alkylcarbamoyl;
$R_2$ is hydrogen;
$R_3$ is hydroxy; and
$R_7$ and $R_8$ are both hydrogen.

A further preferred group of compounds for any feature of the invention include a compound of formula VIII wherein:
$R_1$ is hydrogen or halo or NN—$C_{1-4}$alkylcarbamoyl;
$R_2$ is hydrogen;
$R_3$ is hydroxy; and
$R_7$ and $R_8$ are joined either via a sulphur atom, via —$CH_2$— or via —$C_2H_4$— to form a seven membered sulphur-containing ring, a seven-membered ring or an eight membered ring respectively.

A further preferred group of compounds for any feature of the invention include a compound of formula VIII wherein:
$R_3$ is a group of the formula —E—F—G—H;
E is

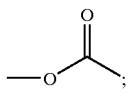

F is a direct bond;
G is $C_{1-4}$alkyl; and
H is hydrogen.

A further preferred group of compounds for any feature of the invention include a compound of formula VIII wherein:
$R_1$ is hydrogen or halo or NN—$C_{1-4}$alkylcarbamoyl;
$R_2$ is hydrogen;
$R_3$ is a group of the formula —E—F—G—H;
E is

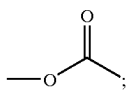

F is a direct bond;
G is $C_{1-4}$alkyl;
H is hydrogen; and
$R_7$ and $R_8$ are both hydrogen.

A further preferred group of compounds for any feature of the invention include a compound of formula VIII wherein:
$R_1$ is hydrogen or halo or NN—$C_{1-4}$alkylcarbamoyl;
$R_2$ is hydrogen;
$R_3$ is a group of the formula —E—F—G—H;
E is

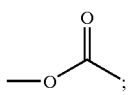

F is a direct bond;
G is $C_{1-4}$alkyl;
H is hydrogen; and
$R_7$ and $R_8$ are joined either via a sulphur atom, via —$CH_2$— or via —$C_2H_4$— to form a seven membered sulphur-containing ring, a seven-membered ring, or an eight membered ring respectively.

A further preferred group of compounds for any feature of the invention include a compound of formula VIII wherein:
$R_4$ is $C_{1-4}$alkyl; and
$R_5$ is phenyl.

A further preferred group of compounds for any feature of the invention include a compound of formula VIII wherein:
$R_1$ is hydrogen or halo or NN—$C_{1-4}$alkylcarbamoyl;
$R_2$ is hydrogen;
$R_3$ is hydrogen halo, hydroxy, or $C_{1-4}$alkoxy;
$R_4$ is $C_{1-4}$alkyl;
$R_5$ is phenyl; and
$R_7$ and $R_8$ are both hydrogen.

A further preferred group of compounds for any feature of the invention include a compound of formula VIII wherein:
$R_1$ is hydrogen or halo or NN—$C_{1-4}$alkylcarbamoyl;
$R_2$ is hydrogen;
$R_3$ is a group of the formula —E—F—G—H;
$R_4$ is $C_{1-4}$alkyl;
$R_5$ is phenyl; and
$R_7$ and $R_8$ are both hydrogen.

A further preferred group of compounds for any feature of the invention include a compound of formula VIII wherein:
$R_1$ is hydrogen or halo or NN—$C_{1-4}$alkylcarbamoyl;
$R_2$ is hydrogen;
$R_3$ is hydrogen halo, hydroxy, or $C_{1-4}$alkoxy;
$R_4$ is $C_{1-4}$alkyl;
$R_5$ is phenyl; and
$R_7$ and $R_8$ are joined either via a sulphur atom, via —$CH_2$— or via —$C_2H_4$— to form a seven membered sulphur-containing ring, a seven-membered ring or an eight membered ring respectively.

A further preferred group of compounds for any feature of the invention include a compound of formula VIII wherein:
$R_1$ is hydrogen or halo or NN—$C_{1-4}$alkylcarbamoyl;
$R_2$ is hydrogen;
$R_3$ is a group of the formula —E—F—G—H;
$R_4$ is $C_{1-4}$alkyl;
$R_5$ is phenyl; and
$R_7$ and $R_8$ are joined either via a sulphur atom, via —$CH_2$— or via —$C_2H_4$— to form a seven membered sulphur-containing ring, a seven-membered ring or an eight membered ring respectively.

A further preferred group of compounds for any feature of the invention include a compound of formula VIII wherein:
$R_6$ is halo, preferably fluoro.

A further preferred group of compounds for any feature of the invention include a compound of formula VIII wherein:
$R_1$ is hydrogen or halo or NN—$C_{1-4}$alkylcarbamoyl;
$R_2$ is hydrogen;
$R_3$ is hydrogen halo, hydroxy, or $C_{1-4}$alkoxy;
$R_6$ is halo, preferably fluoro; and
$R_7$ and $R_8$ are both hydrogen.

A further preferred group of compounds for any feature of the invention include a compound of formula VIII wherein:
$R_1$ is hydrogen or halo or NN—$C_{1-4}$alkylcarbamoyl;
$R_2$ is hydrogen;
$R_3$ is a group of the formula —E—F—G—H;
$R_6$ is halo, preferably fluoro; and
$R_7$ and $R_8$ are both hydrogen.

A further preferred group of compounds for any feature of the invention include a compound of formula VIII wherein:

$R_1$ is hydrogen or halo or NN—$C_{1-4}$alkylcarbamoyl;

$R_2$ is hydrogen;

$R_3$ is hydrogen halo, hydroxy, or $C_{1-4}$alkoxy;

$R_6$ is halo, preferably fluoro; and $R_7$ and $R_8$ are joined either via a sulphur atom, via —$CH_2$— or via —$C_2H_4$— to form a seven membered sulphur-containing ring, a seven-membered ring or an eight membered ring respectively.

A further preferred group of compounds for any feature of the invention include a compound of formula VIII wherein:

$R_1$ is hydrogen or halo or NN—$C_{1-4}$alkylcarbamoyl;

$R_2$ is hydrogen;

$R_3$ is a group of the formula —E—F—G—H;

$R_6$ is halo, preferably fluoro; and $R_7$ and $R_8$ are joined either via a sulphur atom, via —$C_2H_2$— or via —$CH_4$— to form a seven membered sulphur-containing ring, a seven-membered ring or an eight membered ring respectively.

A further preferred group of compounds for any feature of the invention include a compound of formula VIII wherein:

$R_3$ is a group of the formula —E—F—G—H;

E is

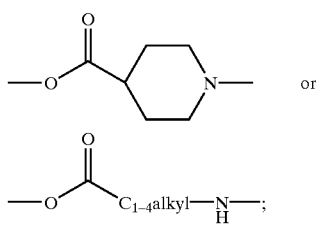

F is

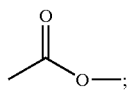

G is $C_{1-4}$alkyl; and

H is phenyl.

A further preferred group of compounds for any feature of the invention include a compound of formula VIII wherein:

$R_1$ is hydrogen or halo or NN—$C_{1-4}$alkylcarbamoyl;

$R_2$ is hydrogen;

$R_3$ is a group of the formula —E—F—G—H;

E is

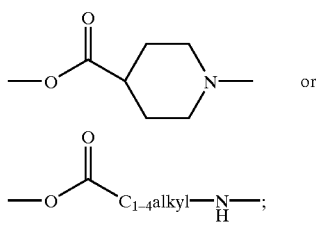

F is

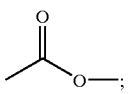

G is $C_{1-4}$alkyl;

H is phenyl; and $R_7$ and $R_8$ are both hydrogen.

A further preferred group of compounds for any feature of the invention include a compound of formula VIII wherein:

$R_1$ is hydrogen or halo or NN—$C_{1-4}$alkylcarbamoyl;

$R_2$ is hydrogen;

$R_3$ is a group of the formula —E—F—G—H;

E is

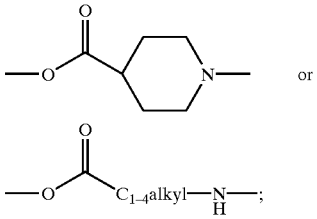

F is

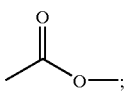

G is $C_{1-4}$alkyl;

H is phenyl; and $R_7$ and $R_8$ are joined either via a sulphur atom, via —$CH_2$— or via —$C_2H_4$— to form a seven membered sulphur-containing ring, a seven-membered ring or an eight membered ring respectively.

A further preferred group of compounds of the invention include a compound of Formula VIII wherein:

$R_1$ is selected from hydrogen or NN-di-$C_{1-4}$alkylcarbamoyl;

D is selected from $C_{1-4}$alkylene or $C_{1-4}$alkenylene;

$R_2$ is hydrogen;

$R_3$ is selected from hydrogen, hydroxyl, $C_{1-4}$alkoxy or a group of the formula —E—F—G—H.

$R_4$ and $R_5$ each represent $C_{1-4}$alkyl, $R_4$ represents $C_{1-4}$alkyl and $R_5$ represents phenyl or together $R_4$ and $R_5$ form a pyrrolidino ring;

$R_6$ is selected from hydrogen, $C_{1-4}$alkyl or halo;

$R_7$ and $R_8$ are either both hydrogen or when A is of Formula X may be joined either via a sulphur atom, via —$CH_2$— or via —$C_2H_4$— to form a seven membered sulphur-containing ring, a seven-membered ring or an eight membered ring respectively;

$R_9$ is hydrogen or $C_{1-4}$alkyl; and $R_{10}$ is hydrogen.

or a pharmaceutically acceptable salt, prodrug or solvate thereof.

A further preferred group of compounds for any feature of the invention include a compound of formula VIII wherein:

$R_1$ is hydrogen;

D is selected from $C_{1-4}$alkylene or $C_{1-4}$alkenylene, preferably $C_{1-2}$alkylene or $C_{1-3}$alkenylene, most preferably ethylene or 2-propenylene;

$R_2$ is hydrogen;

$R_3$ is selected from hydrogen, hydroxyl, $C_{1-4}$alkoxy or a group of the formula —E—F—G—H. Preferably hydrogen, hydroxyl or $C_{1-4}$alkoxy. Most preferably hydrogen or hydroxy;

$R_4$ and $R_5$ each represent $C_{1-4}$alkyl, $R_4$ represents $C_{1-4}$alkyl and $R_5$ represents phenyl or together $R_4$ and $R_5$ form a pyrrolidino ring. Preferably $R_4$ and $R_5$ each represent methyl or ethyl. $R_4$ represents $C_{1-2}$alkyl and $R_5$ represents phenyl or together $R_4$ and $R_5$ form a pyrrolidino ring. Most preferably $R_4$ and $R_5$ each represent methyl or ethyl or together $R_4$ and $R_5$ form a pyrrolidino ring;

$R_6$ is selected from hydrogen $C_{1-4}$alkyl or halo. More preferably $R_6$ is hydrogen, C1–2alkyl or halo. Most preferably $R_6$ is hydrogen, methyl, ethyl or fluoro;

$R_7$ is hydrogen;

$R_8$ is hydrogen;

$R_9$ is hydrogen; and $R_{10}$ is hydrogen.

or a pharmaceutically acceptable salt, prodrug or solvate thereof

A further preferred group of compounds for any feature of the invention include a compound of formula VIII wherein:

$R_1$ is hydrogen;

D is selected from $C_{1-4}$alkylene or $C_{1-4}$alkenylene, preferably $C_{1-2}$alkylene or $C_{1-3}$alkenylene, most preferably ethylene or 2-propenylene;

$R_2$ is hydrogen;

$R_3$ is selected from hydrogen, hydroxyl, $C_{1-4}$alkoxy or a group of the formula —E—F—G—H. Preferably hydrogen, hydroxyl or $C_{1-4}$alkoxy. Most preferably hydrogen or hydroxy;

$R_4$ and $R_5$ each represent $C_{1-4}$alkyl, $R_4$ represents $C_{1-4}$alkyl and $R_5$ represents phenyl or together $R_4$ and $R_5$ form a pyrrolidino ring. Preferably $R_4$ and $R_5$ each represent methyl or ethyl. $R_4$ represents $C_{1-2}$alkyl and $R_5$ represents phenyl or together $R_4$ and $R_5$ form a pyrrolidino ring. Most preferably $R_4$ and $R_5$ each represent methyl or ethyl or together $R_4$ and $R_5$ form a pyrrolidino ring;

$R_6$ is selected from hydrogen $C_{1-4}$alkyl or halo. More preferably $R_6$ is hydrogen, C1–2alkyl or halo. Most preferably $R_6$ is hydrogen, methyl, ethyl or fluoro;

$R_7$ is hydrogen;

$R_8$ is hydrogen;

$R_9$ is hydrogen; and $R_{10}$ is hydrogen.

With the proviso that when D is $C_{1-4}$alkyl then $R_3$ or $R_6$ must be other than hydrogen, or $R_4$ and $R_5$ must be other than each independently $C_{1-4}$alkyl.

or a pharmaceutically acceptable salt, prodrug or solvate thereof

Preferred compounds for any feature of the invention include: tamoxifen (preferably in the form of tamoxifen citrate), droloxifene, toremifene, idoxifene and TAT 59 (miproxifene).

Further preferred compounds for any feature of the invention include:

(1) 4-[2-(3-chlorophenyl)-1-[4-[2-(dimethylamino)ethoxy]phenyl]-1-butenyl]-Phenol;

(2) 2-[p-[1,2-bis(p-chlorophenyl)-1-butenyl]phenoxy]-N,N-dimethyl-Ethylamine;

(3) 2-[(6-ethyl-11,12-dihydro-5-phenyldibenzo[a,e]cycloocten-2-yl)oxy]-N,N-dimethyl-Ethanamine;

(4) 4-[2-[2-(dimethylamino)ethoxy]-6-ethyl-11,12-dihydrodibenzo[a,e]cycloocten-5-yl-Phenol;

(5) 2-[(10-ethyl-11-phenyldibenzo[b,f]thiepin-3-yl)oxy]-N,N-dimethyl-, Ethanamine;

(6) 4-[7-[2-(dimethylamino)ethoxy]-11-ethlydibenzo[b,f]thiepin-10-yl]-, Phenol;

(7) 4-[1-[4-[2-(dimethylamino)ethoxy]phenyl]-2-phenyl-1-butenyl]-, 1,2-Benzenediol;

(8) 2-[4-[(1Z)-4-chloro-1,2-diphenyl-1-butenyl]phenoxy]-N,N-dimethyl-, Ethanamine;

(9) 2-[4-[1-(4-fluorophenyl)-2-phenyl-1-butenyl]phenoxy]-N,N-dimethyl-, Ethanamine;

(10) 4-[1-[4-[2-(dimethylamino)ethoxy]phenyl]-2-phenyl-1-butenyl]phenyl, Benzeneacetic acid ester;

(11) methoxy-, 4-[1-[4-[2-(dimethylamino)ethoxy]phenyl]-2-phenyl-1-butenyl]phenyl ester, Acetic acid;

(12) propyl-, 4-[1-[4-[2-(dimethylamino)ethoxy]phenyl]-2-phenyl-1-butenyl]phenyl ester, Carbamic acid;

(13) 4-[1-[4-[2-(dimethylamino)ethoxy]phenyl]-2-phenyl-1-butenyl]-Phenol phenylcarbamate (ester)

(14) 4-bromo-, 4-[1-[4-[2-(dimethylamino)ethoxy]phenyl]-2-phenyl-1-butenyl]phenyl ester, Benzoic acid;

(15) 4-[1-[4-[2-(dimethylamino)ethoxy]phenyl]-2-phenyl-1-butenyl]-,Phenol, benzoate (ester);

(16) 4-[1-[4-[2-(dimethylamino)ethoxy]phenyl]-2-phenyl-1-butenyl]-Phenol acetate (ester);

(17) 2-[4-(1,2-diphenyl-1-butenyl)phenoxy]-N,N-dimethyl-Ethanamine;

(18) 1-[2-[4-(1,2-diphenyl-1-butenyl)phenoxy]ethyl]-Piperidine and

(19) 4-[1-[4-[2-(dimethylamino)ethoxy]phenyl]-2-phenyl-1-butenyl]phenyl ester, 2,4,6-Trimethyl-benzoic acid.

More further preferred compounds for any feature of the invention include:

(21) 4-[2-phenyl-1-[4-[2-(1-pyrrolidinyl)ethoxy]phenyl]-1-butenyl]-, Phenol;

(22) 2,2-dimethyl-, 4-[1-[4-[2-(dimethylamino)ethoxy]phenyl]-2-phenyl-1-butenyl]phenyl ester, Propanoic acid;

(23) 4-[1-[4-[2-(dimethylamino)ethoxy]phenyl]-2-phenyl-1-butenyl]-, Phenol;

(24) 1-[2-[p-[.beta.-ethyl-.alpha.-(p-methoxyphenyl)styryl]phenoxy]ethyl]-, Pyrrolidine;

(26) 2-[p-(1,2,3-triphenylpropenyl)phenoxy]-, Triethylamine;

(27) 2-[4-[1-(2-ethylphenyl)-2-phenyl-1-butenyl]phenoxy]-N,N-dimethyl-, Ethanamine;

(28) 2-[(10-(NN-diethylpropanamido)-11-phenyldibenzo[b,f]thiepin-3-yl)oxy]-N,N-dimethyl-Ethanamine;

(29) 2-[4-(1,2-diphenyl-1-butenyl)phenoxy]-N-methyl-N-phenyl-, Ethanamine;

(30) 2-[4-[1-phenyl-2-(4-fluorophenyl)-1-butenyl]phenoxy]-N,N-dimethyl-, Ethanamine;

(31) 3-amino-, 4-[1-[4-[2-(dimethylamino)ethoxy]phenyl]-2-phenyl-1-butenyl]phenyl ester, Benzoic acid;

(32) 1-benzyl 4-[4-(1-4-[2-(dimethylamino)ethoxy]phenyl-2-phenyl-1-butenyl)phenyl]tetrahydro-1,4(2H)-pyridinedicarboxylate; and

(33) 4-(1-4-[2-(dimethylamino)ethoxy]phenyl-2-phenyl-1-butenyl)phenyl 2-[(benzyloxy)carbonyl]aminoacetate.

Most preferred compounds for any feature of the invention include:

(20) 4-[1-[4-[2-(dimethylamino)ethoxy]phenyl]-2-(4-ethylphenyl)-1-butenyl]-, Phenol;
(25) 2-[p-(1,2-diphenyl-1,4-pentadienyl)phenoxy]-Triethylamine;

Compounds for use in any feature of the invention can exist in both the (E)- and (Z)-isomeric configuration related to the proximity of groups across the double bond in compounds of Formula I and Formula VIII. Compounds of the invention are active in both their (E)- and (Z)-configurations. Preferred orientations in the numbered compounds above are:
(Z)- (1), (12), (13), (14), (17), (19), (20), (23), (26), (27), (29), (31);
(E)- (7), (8), (9), (10), (11), (15), (16), (18), (21), (22), (24), (25), (30), (32), (33).

According to another aspect of the invention there is provided a compound selected from:

(34) 4-[1-[4-[2-(dimethylamino)ethoxy]phenyl]-2-phenyl-1-butenyl]phenyl ester, 2,4,6-Trimethyl-benzoic acid
(35) 2-[4-[1-(2-ethylphenyl)-2-phenyl-1-butenyl]phenoxy]-N,N-dimethyl-, Ethanamine
(36) 2-[(10-(NN-diethylpropanamido)-11-phenyldibenzo[b,f]thiepin-3-yl)oxy]-N,N-dimethyl-Ethanamine
(37) [4-(1,2-diphenyl-1-butenyl)phenoxy]-N-methyl-N-phenyl-, Ethanamine
(38) [4-[1-phenyl-2-(4-fluorophenyl)-1-butenyl]phenoxy]-N,N-dimethyl-, Ethanamine
(39) 3-amino-, 4-[1-[4-[2-(dimethylamino)ethoxy]phenyl]-2-phenyl-1-butenyl]phenyl ester, Benzoic acid
(40) 1-benzyl 4-[4-(1-4-[2-(dimethylamino)ethoxyphenyl-2-phenyl-1-butenyl)phenyl]tetrahydro-1,4(2H)-pyridinedicarboxylate
(41) (1-4-[2-(dimethylamino)ethoxy]phenyl-2-phenyl-1-butenyl)phenyl 2-[(benzyloxy)carbonyl]aminoacetate
or salts, prodrugs or solvates thereof Preferred orientations in the numbered compounds of this further aspect of the invention above are:
(Z)- (34), (35), (37), (39);
(E)- (38), (40), (41).

According to another feature of the invention there is provided a pharmaceutical composition comprising a compound of the invention or a pharmaceutically acceptable salt, prodrug or solvate thereof, in association with a pharmaceutically acceptable excipient or carrier.

According to a further aspect of the present invention there is provided a method of treating or preventing cognitive disorders, such as Alzheimer's disease, vascular dementia and age-related dementia, in a warm-blooded mammal, such as man, which comprises administering an effective amount of a compound of the invention described herein or a pharmaceutically acceptable salt, prodrug or solvate thereof.

In a further feature of the invention there is provided a method of treating or preventing Alzheimer's disease or vascular dementia in a warm blooded mammal, such as man, which comprises administering an effective amount of a compound of the invention described herein or a pharmaceutically acceptable salt, prodrug or solvate thereof.

In a further feature of the invention there is provided a method of preventing or inhibiting ischemia-induced neurodegeneration in a warm-blooded mammal which comprises administering a compound of the invention described herein, or a pharmaceutically acceptable salt, prodrug or solvate thereof.

In a further feature of the invention there is provided a method of preventing or inhibiting the formation of β-amyloid plaques or neurofibrillary tangles in the brain in a warm-blooded mammal comprising administering an effective amount of a compound of the invention described herein, or a pharmaceutically acceptable salt, prodrug or solvate thereof.

In a further feature of the invention there is provided a method of inhibiting or preventing the inflammatory response associated with Alzheimer's Disease in a warm blooded mammal comprising administering an effective amount of a compound of the invention described herein, or a pharmaceutically acceptable salt, prodrug or solvate thereof.

In a further feature of the invention there is provided a method of treating stroke, head trauma or spinal cord injury in a warm blooded mammal comprising administering an effective amount of a compound of the invention described herein, or a pharmaceutically acceptable salt, prodrug or solvate thereof.

According to a further feature of the current invention there is provided the use of a compound of the invention described herein, or a pharmaceutically acceptable salt, prodrug or solvate thereof, for the manufacture of a medicament for the treatment of neurological disorders in a warm blooded mammal.

According to a further feature of the current invention there is provided the use of a compound of the invention described herein, or a pharmaceutically acceptable salt, prodrug or solvate thereof, for the manufacture of a medicament for the treatment of cognitive disorders, such as Alzheimer's disease, vascular dementia or age-related dementia in a warm blooded mammal.

According to a further feature of the current invention there is provided the use of a compound of the invention described herein, or a pharmaceutically acceptable salt, prodrug or solvate thereof, for the manufacture of a medicament for the prevention of or the inhibition of ischemia-induced neurodegeneration in a warm blooded mammal.

According to a further feature of the current invention there is provided the use of a compound of the invention described herein, or a pharmaceutically acceptable salt, prodrug or solvate thereof, for the manufacture of a medicament for the prevention of or the inhibition of the formation of β-amyloid plaques or neurofibrillary tangles in the brain in a warm blooded mammal.

According to a further feature of the current invention there is provided the use of a compound of the invention described herein, or a pharmaceutically acceptable salt, prodrug or solvate thereof, for the manufacture of a medicament for the prevention of or the inhibition of the inflammatory response associated with Alzheimer's Disease in a warm blooded mammal.

According to a further feature of the current invention there is provided the use of a compound of the invention described herein, or a pharmaceutically acceptable salt, prodrug or solvate thereof, for the manufacture of a medicament for the treatment of stroke, head trauma or spinal cord injury.

According to a further feature of the current invention there is provided a pharmaceutical composition comprising a compound of the invention described herein, or a pharmaceutically acceptable salt, prodrug or solvate thereof, in admixture with a pharmaceutically-acceptable diluent or carrier for the prevention or treatment of neurological disorders in a warm blooded mammal.

According to a further feature of the current invention there is provided a pharmaceutical composition comprising a compound of the invention described herein, or a pharmaceutically acceptable salt, prodrug or solvate thereof, in admixture with a pharmaceutically-acceptable diluent or carrier for the prevention or treatment of cognitive disorders, such as Alzheimer's disease, vascular dementia or age-related dementia in a warm blooded mammal.

According to a further feature of the current invention there is provided a pharmaceutical composition comprising a compound of the invention described herein, or a pharmaceutically acceptable salt, prodrug or solvate thereof, in admixture with a pharmaceutically-acceptable diluent or carrier for the prevention of or the inhibition of ischemia-induced neurodegeneration in a warm-blooded mammal.

According to a further feature of the current invention there is provided a pharmaceutical composition comprising a compound of the invention described herein, or a pharmaceutically acceptable salt, prodrug or solvate thereof, in admixture with a pharmaceutically-acceptable diluent or carrier for the prevention of or the inhibition of the formation of β-amyloid plaques or neurofibrillary tangles in the brain in a warm blooded mammal.

According to a further feature of the current invention there is provided a pharmaceutical composition comprising a compound of the invention described herein, or a pharmaceutically acceptable salt, prodrug or solvate thereof, in admixture with a pharmaceutically-acceptable diluent or carrier for the prevention of or the inhibition of the inflammatory response associated with Alzheimer's Disease in a warm blooded mammal.

According to a further feature of the current invention there is provided a pharmaceutical composition comprising a compound of the invention described herein, or a pharmaceutically acceptable salt, prodrug or solvate thereof, in admixture with a pharmaceutically-acceptable diluent or carrier for the treatment of stroke, head trauma or spinal cord injury.

According to a further feature of the current invention there is provided a method of treating or preventing neuronal apoptosis and/or excitotoxicity related neurological disorders in a warm-blooded mammal which comprises administering to said warm-blooded mammal an effective amount of a compound of the invention described herein or a pharmaceutically acceptable salt, prodrug or solvate thereof.

According to a further feature of the current invention there is provided the use of a compound of the invention described herein or a pharmaceutically acceptable salt, prodrug or solvate thereof, for the manufacture of a medicament for the treatment or prevention of neuronal apoptosis and/or excitotoxicity related neurological disorders in a warm blooded mammal.

According to a further feature of the current invention there is provided a pharmaceutical composition comprising a compound of the invention described herein or a pharmaceutically acceptable salt, prodrug or solvate thereof for the prevention or treatment of neuronal apoptosis and/or excitotoxicity related neurological disorders in a warm blooded mammal.

According to a further feature of the invention there is provided the use of a compound, which has a high affinity for the emopamil binding protein and inhibits neuronal apoptosis and/or neuronal excitotoxicity, for the treatment or prevention of neurological disorders.

According to a further feature of the invention there is provided the use of a compound, which has a high affinity for the emopamil binding protein and inhibits neuronal apoptosis, for the treatment or prevention of neurological disorders.

According to a further feature of the invention there is provided the use of a compound, which has a high affinity for the emopamil binding protein and inhibits neuronal excitotoxicity, for the treatment or prevention of neurological disorders.

The methods of treatment, compositions or medicaments may be used to treat patients who exhibit neurological disorders in order to at least ameliorate symptoms of such disorders and/or to treat patients prophylactically to prevent or inhibit onset of neurological disorders in patients who have a susceptibility to developing such disorders.

The expression "neurological disorders" includes to cognitive disorders, neuronal apoptosis, excitotoxicity and/or disorders which comprise neuronal apoptosis and/or excitotoxicity as part of their pathology.

Such "neurological disorders include, but are not limited to, Alzheimer's disease, vascular dementia and age-related dementia as well as head trauma, stroke, spinal cord injury, amyotrophic lateral sclerosis (ALS), Parkinson's disease, Huntington's chorea, AIDS-related dementia, peripheral neuropathies and macular degeneration.

The expression "neuronal apoptosis and/or excitotoxicity related neurological disorders" as used herein means neurological disorders in which either neuronal apoptosis or excitotoxicity are implicated as a pathological process in said neurological disorders or both neuronal apoptosis and excitotoxicity are implicated as a pathological process in said neurological disorders.

The term 'tamoxifen' as used herein includes tamoxifen and it is physiologically compatible salts, but is preferably used to refer to tamoxifen citrate.

The term cognitive disorder means any disturbance of normal function related to the mental activities associated with thinking, learning and memory, or any process whereby one acquires knowledge.

The term "inhibit" includes its generally accepted meaning which includes prohibiting, preventing, restraining, and slowing, stopping, or reversing progression, severity, or a resultant symptom or effect.

The term "effective amount" means the amount of compound necessary to inhibit or prevent a cognitive disorder such as Alzheimer's Disease or any of its symptoms, inhibit of prevent ischemia-induced neurodegeneration, inhibit or prevent beta -amyloid peptide mediated neurotoxicity or inhibit or prevent the inflammatory response associated with Alzheimer's Disease, as the case may be.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

Processes for producing the preferred compounds of the invention and other tamoxifen analogues are detailed in the following patents: toremifene (U.S. Pat. No. 5,491,173, U.S.

Pat. No. 4,996,225), droloxifene (U.S. Pat. No. 5,047,431), TAT 59 (U.S. Pat. No. 4,897,503) and idoxifene (U.S. Pat. No. 4,839,155), each incorporated by reference herein.

The compounds used in the methods of the current invention, wherein both $R_7$ and $R_8$ are both hydrogen, are made according to the general procedures as follows: Briefly the starting compound of Formula II,

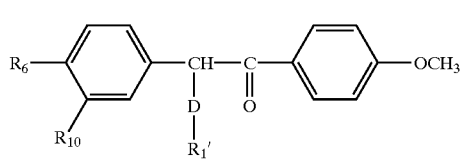

Formula II wherein $R_1'$ is hydrogen, D and $R_6$ are as described above, is demethylated with a boron trihalide at between 0° C. and room temperature, typically using methylene chloride as solvent. The product of this reaction is then reacted with a compound of the general formula:

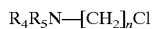

$R_4R_5N$—$[CH_2]_n$Cl wherein $R_4$, $R_5$ and n are as described above, conveniently in the presence of a base, to give a compound of formula III:

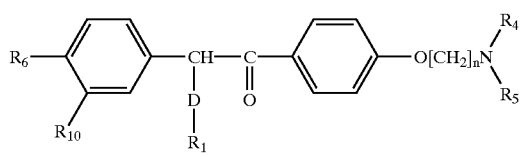

Formula III

The compound of Formula III is further reacted by a Grignard reaction in an inert solvent with a phenylmagnesiumhalide derivative of the formula:

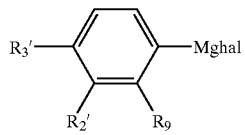

or with a organometallic halobenzene species of the formula:

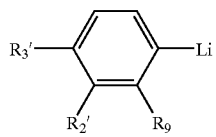

in which $R_2$ is hydrogen, $C_{1-4}$alkyl or a protected hydroxyl group and $R_3$, is either hydrogen, a protected hydroxyl, alkoxy or halo, to produce a compound of Formula IV:

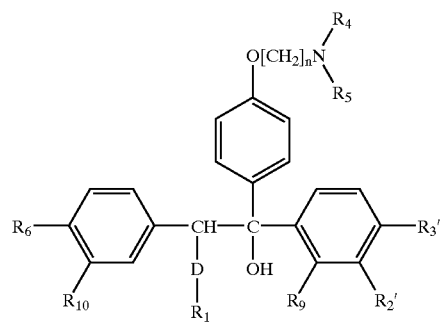

Formula IV

The hydroxyl protecting group could typically be tetrahydopyranyl (thp). The compound of Formula IV is then dehydrated using an appropriate acid catalyst, for example hydrochloric acid, in an appropriate solvent, for example ethanol, to produce a mixture of cis and trans isomers which can be separated by fractional crystallization or chromatography to yield the cis or trans isomer of Formula I or Formula VIII. Under the dehydration conditions the thp protecting group will also be removed.

For the formation of compounds used in the methods of the invention wherein $R_7$ and $R_8$ are joined either via a sulphur atom, via —$CH_2$— or via —$C_2H_4$— to form a seven membered sulphur-containing ring, a seven-membered ring, or an eight membered ring respectively and A is of Formula X, a compound of Formula XI is used.

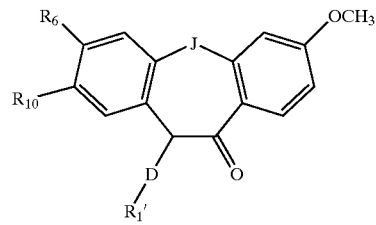

Formula XI wherein $R_1'$ is hydrogen, J is a group of the formula, —S—, —$CH_2$— or —$CH_2CH_2$— and D and $R_6$ are as defined above. For the synthesis of a compound of Formula XI the reader is referred to Acton et al [1983] J. Med Chem. 26, 1131–1137.

A compound of formula XI may be de-methylated as described above and then reacted with a compounds of the general formula:

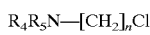

$R_4R_5N$—$[CH_2]_n$Cl to form a compound of Formula XII.

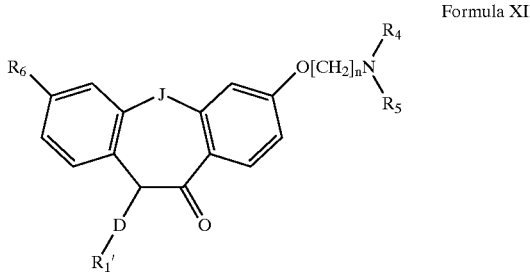

Formula XII

The compound of Formula XII is further reacted by a Grignard reaction in an inert solvent with a phenylmagnesiumhalide derivative of the formula:

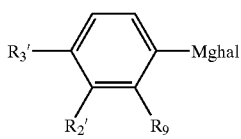

or with a organometallic halobenzene species of the formula:

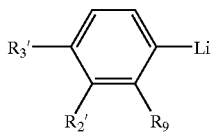

in which $R_2$, is hydrogen, $C_{1-4}$alkyl or a protected hydroxyl group and $R_3$, is either hydrogen, a protected hydroxyl or halo, to produce a compound of Formula XIII:

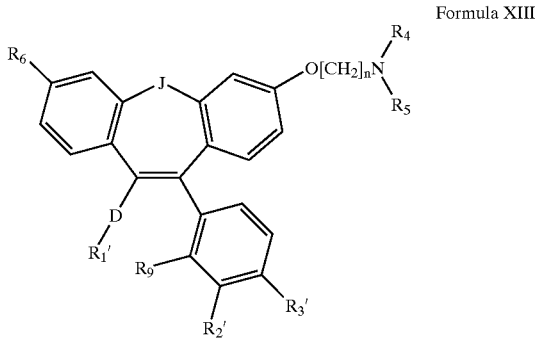

Formula XIII

A analogous series of reactions can be used to synthesise compounds of the invention wherein Formula X is of the Formula Xa.

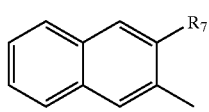

Formula Xa

For the formation of compounds of the invention which have a $PO_4$ group at $R_3$, $R_3$, is a protected hydroxyl group. At the end of the synthesis, after the deydration step and separation of the cis isomer of Formula I, the hydroxyl group is phosphorylated. Usable as phosphorylating groups are, for example, phosphorous oxyhalides such as phosphorous oxychloride and phosporous oxychloride, phosphoric acid anhydrides such as pyrophosphonic acid and polyphosphoric acid. Among these preferred is phosphorous oxychloride. A suitable solvent for this reaction in one which activates the phosphorylating group and does not interfere with the reaction. Suitable solvents include pyridine, tetrahydrofuran and acetonitrile. For information relating the phosphorylation conditions the reader is referred to U.S. Pat. No. 4,897,503.

For the formation of compounds used in the methods of the invention wherein $R_3$ is of the formula:

and E is selected from:

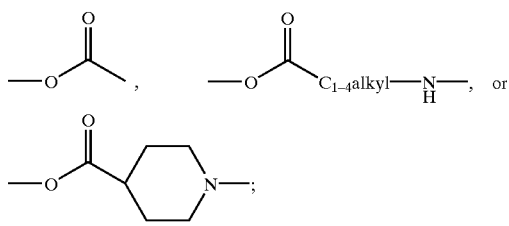

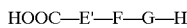

a compound of Formula I or Formula VIII wherein $R_3$ is a hydroxyl may be acylated with an acylating derivative obtained from an acid of the formula:

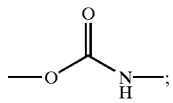

wherein E is the group E without the oxygen and carboxyl on the left of the group or when E is a group of the formula:

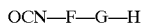

may be reacted with an isocyanate of the formula:

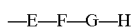

Compounds used in the methods of the invention wherein $R_3$ is of the formula:

—E—F—G—H and E is selected from:

can be made from a compound of Formula XIV wherein the A, B, D, $R_2$, $R_4$, $R_5$, $R_8$ and $R_9$ are as in herein before defined.

Formula XIV

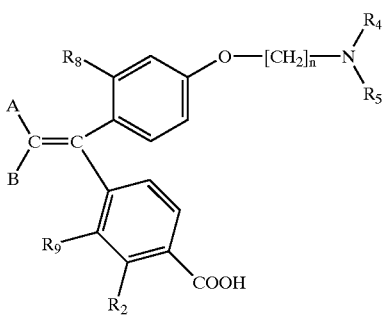

Formula VI

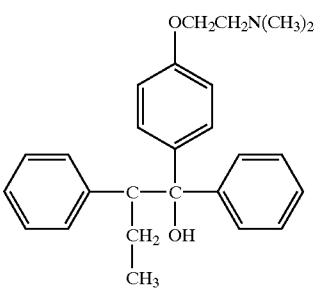

A chemist skilled in the art would be able to synthesise the respective acid or isocyanate derivatives of the group —E—F—G—H to be used in coupling to a compound of Formula I or Formula VIII wherein $R_3$ is a hydroxyl.

Compounds used in methods of the invention wherein $R_1$ is halo can be prepared from a compound of Formula XV or the corresponding derivative of Formula XI, wherein $R_6$ and $R_{10}$ are as herein before defined and $R_{11}$ is a protecting group.

Formula XV

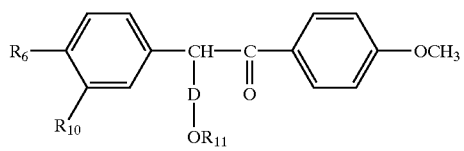

to form the corresponding compound of Formula I or Formula VIII wherein $R_1$ is hydroxyl. This can then be converted by various methods to a compound of Formula I or Formula VIII wherein $R_1$ is halo.

Compounds used in methods of the invention wherein $R_1$ is, carbamoyl, N—$C_{1-4}$alkylcarbamoyl or NN-di-$C_{1-4}$alkylcarbamoyl can be prepared from the appropriate carboxylic acid using ammonia, or the appropriate primary or secondary amine.

The reader is referred to Protective Groups in Organic synthesis, $2^{nd}$ Edition, by Green et al., published by John Wiley & Sons for general guidance on protecting groups.

Specifically tamoxifen can be produced as detailed in U.S. Pat. No. 4,536,516. Briefly the process starts with (α-ethyl-4-methoxydesoxybenzoin which is demethylated with pyridine hydrochloride at high temperature to give 4-hydroxy-α-ethyldesoxybenzoin. The sodium salt of the latter compound is then reacted with β-dimethylaminoethyl chloride to form a compound of Formula V:

Formula V

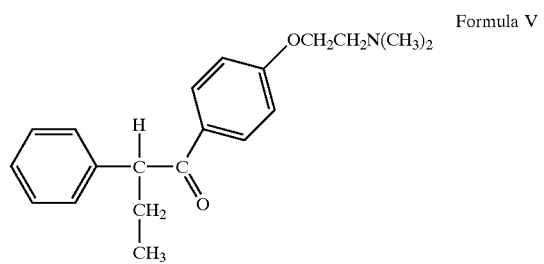

Formula II is then reacted with the Grignard reagent, phenyl magnesium bromide in an inert solvent to give a compound of formula VI.

Dehydration of the alkanol of Formula III is then carried out via reaction with an acid catalyst, for example hydrochloric acid, in a solvent for example ethanol with the application of heat. The dehydration of formula III yields a mixture of cis and trans isomers which can be separated by fractional crystallization to give the cis isomer of formula I.

Alternative methods for the production of Formula VII can be found in U.S. Pat. No. 4,960,937, incorporated by reference herein where $R_2$ is as defined above.

Formula VII

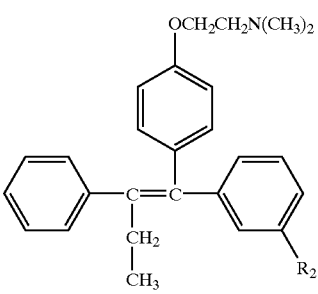

The present invention relates to the compounds of Formula I or Formula VIII as hereinbefore defined as well as to the salts thereof. Salts for use in pharmaceutical compositions will be pharmaceutically acceptable salts, but other salts may be useful in the production of the compounds of formula I and their pharmaceutically acceptable salts. A suitable pharmaceutically-acceptable salt of a compound of the Formula I or Formula VIII is, for example, an acid-addition salt of a compound of the Formula I or Formula VIII which is sufficiently basic, for example an acid-addition salt with an inorganic or organic acid such as hydrochloric, hydrobromic, sulphuric, trifluoroacetic, citric or maleic acid; or, for example a salt of a compound of the Formula 1 or Formula VIII which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Various forms of prodrugs are known in the art. For examples of such prodrug derivatives, see:
  a) Design of Prodrugs, edited by H. Bundgaard, (Elsevier, 1985) and Methods in Enzymology, Vol.42, p. 309–396, edited by K. Widder, et al. (Academic Press, 1985);
  b) A Textbook of Drug Design and Development, edited by Krogsgaard-Larsen and H. Bundgaard, Chapter 5 "Design and Application of Prodrugs", by H. Bundgaard p. 113–191 (1991);
  c) H. Bundgaard, Advanced Drug Delivery Reviews, 8, 1–38 (1992);

d) H. Bundgaard, et al., Journal of Pharmaceutical Sciences, 77, 285 (1988); and e) N. Kakeya, et al., Chem Pharm Bull, 32, 692 (1984).

Examples of such pro-drugs may be used to form in vivo cleavable esters of a compound of the Formula (1). An in vivo cleavable ester of a compound of the Formula (1) containing a carboxy group is, for example, a pharmaceutically-acceptable ester which is cleaved in the human or animal body to produce the parent acid. Suitable pharmaceutically-acceptable esters for carboxy include $C_{1-6}$alkoxymethyl esters, for example methoxymethyl; $C_{1-6}$alkanoyloxymethyl esters, for example pivaloyloxymethyl; phthalidyl esters; $C_{3-8}$cycloalkoxycarbonyloxy$C_{1-6}$alkyl esters, for example 1-cyclohexylcarbonyloxyethyl; 1,3-dioxolan-2-ylmethyl esters, for example 5-methyl-1,3-dioxolan-2-ylmethyl; and $C_{1-6}$alkoxycarbonyloxyethyl esters, for example 1-methoxycarbonyloxyethyl; and may be formed at any carboxy group in the compounds of this invention.

It will also be understood that certain compounds of the present invention may exist in solvated, for example hydrated, as well as unsolvated forms. It is to be understood that the present invention encompasses all such solvated forms which possess the properties of inhibiting or preventing cognitive disorders, inhibiting or preventing ischemia-induced neurodegeneration, inhibiting or preventing the formation of β-amyloid plaques or neurofibrillary tangles in the brain, or inhibiting or preventing the inflammatory response associated with Alzheimer's.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

Frequently, it will be desirable or necessary to introduce the pharmaceutical compositions directly or indirectly to the brain. Direct techniques usually involve placement of a drug delivery catheter into the host's ventricular system to bypass the blood-brain barrier. Indirect techniques, which are generally preferred, involve formulating the compositions to provide for drug latentiation by the conversion of hydrophilic drugs into lipid-soluble drugs. Latentiation is generally achieved through blocking of the hydroxyl, carboxyl, and primary amine groups present on the drug to render the drug more lipid soluble and amenable to transportation across the blood-brain barrier. Alternatively, the delivery of hydrophilic drugs can be enhanced by intra-arterial infusion of hypertonic solutions which can transiently open the blood-brain barrier.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I or Formula VIII will naturally vary according to the nature and severity of the conditions, the age and sex of the animal or patient and the route of administration, according to well known principles of medicine.

In using a compound of the Formula I or Formula VIII for therapeutic or prophylactic purposes it will generally be administered so that a daily dose in the range, for example, 0.1 mg to 1000 mg per day is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred, particularly in tablet form. The unit dosage forms will contain about 1 mg to 500 mg of a compound of this invention, more typically the dosage form would contain between 1 mg and 50 mg. Compounds of Formula I or Formula VIII are preferably administered orally, conveniently in a dosage of 10–40 mg daily.

The compounds of this invention may be used in combination with other drugs and therapies used in the treatment or prevention of cognitive disorders such as Alzheimer's disease, vascular dementia or, less preferably, age-related dementia.

If formulated as a fixed dose such combination products employ the compounds of this invention within the dosage range described herein and the other pharmaceutically-active agent within its approved dosage range. Sequential use is contemplated when a combination formulation is inappropriate.

The invention will now be illustrated with reference to the following non-limiting examples.

The displacement of $^3$H-emopamil binding assay, the NMDA-induced neuronal dealth model and the inhibition of apoptosis in PC12 cells are all standard assays/models recognised in the medical community as indicative of efficacy.

Compounds that bind with high affinity to the 3H-emopamil binding protein have been shown to be neuroprotective in animal models of cerebral ischemia. As the emopamil binding protein has been shown to be the mammalian homolog of delta-8, delta-7 sterol isomerase, it has been suggested that the neuroprotective mechanism of high affinity 3H-emopamil binding site ligands results from the inhibition of de novo cholesterol metabolism. Inhibition of cholesterol metabolism may alter the processing of amyloid precursor protein in a manner that would be expected to delay the progression of Alzheimer's disease pathophysiology. Therefore, high affinty 3H-emopamil binding site ligands that inhibit the de novo synthesis of cholesterol would be expected to alleviate ischemia induced neurodegeneration and inhibit the pathophysiological progression of Alzheimer's disease. [See: Moebius et al., Trends Pharmacol Sci 18:67–70, 1997; Racchi et al., Biochem J 322:893–898, 1997; Silve et al., Mol. Cell. Biol. 16:2719–2727, 1996].

NMDA-induced neuronal death is a model of excitotoxicity that is reflective of death induced by necrosis. During cerebral ischemic events there is excessive release of glutamate, the endogenous NMDA receptor agonist, that results in neuronal cell death due predominantly to necrotic mechanisms. Compounds that inhibit NMDA receptor function are active in experimental models of ischemia that are thought to be most reflective of the clinical situation, and a number of these compounds are in clinical trial evaluation for the treatment of stroke. Recurrent ischemic events are the proximal cause of dementia in vascular dementia, and ischemia-induced neurodegeneration severely exacerbates the cognitive decline that is associated with Alzheimer's disease pathphysiology. Therefore, drugs that inhibit NMDA receptor function would be expected to preserve neurons in stroke, and prevent ischemia induced cognitive decline that is observed in vascular dementia and Alzheimer's disease. [See: Gotti et al., Brain Research 522:290–307, 1990; Gwag et al., Neuroscience 68:615–619, 1995; Koroshetz and Moskowitz, Trends in Pharmacological Sci. 17:227–233, 1996;

Snowdon et al., JAMA, 277:813–817, 1997].

Nerve growth factor withdrawal in differentiated PC12 cells is a model of neuronal death induced by apoptosis. Neurodegeneration resulting from apoptotic mechanisms has been implicated in a number of disease processes, including stroke, traumatic brain injury, Alzheimer's disease, Parkinson's disease, amyotrophic lateral sclerosis, vascular dementia, AIDS related dementia and macular degeneration. Therefore, compounds that are active in inhibiting, apoptosis in PC12 cells would be expected to alleviate the neuronal death associated with apoptosis in these neurological disorders [See: Barinaga, Science 281:1303–1304, 1998;

Kusiak et al., Molecular and Chemical Neuropathology 28:153–162, 1996; Spence et al., Exp. Opin. Ther. Patents 6:345–366, 1996; Charriaut-Marlangue et al., TINS 19:109–114, 1996; von Bartheld, Histology and Histopathology, 13:437–459, 1998; Hara et al., Proc. Natl. Acad. Sci., USA 94:2007–2012, 1997; Yakovlev, et al., J. Neuroscience 17:7415–7424, 1997].

Neuronal cell death in stroke, Alzheimer's disease, Parkinson's disease and other neurological disorders is believed to occur as a result of pathophysiological mechanisms associated with both apoptosis and necrosis, and may depend on the severity of neuronal insult. While pharmacological approaches that inhibit either necrosis or apoptosis would be expected to offer some benefit, this benefit may be limited due to incomplete inhibition of the pathways that lead to neuronal cell death. For example, neurotrophic factors that inhibit neuronal apoptosis exacerbate excitotoxicity induced by NMDA receptor activation. It is thus possible that preventing apoptosis may ultimately result in increased necrotic cell death. Optimal neuroprotective approaches may therefore be those that can inhibit both apoptosis and necrosis. In this regard, compounds of Formula I or Formula VIII, especially tamoxifen citrate, has have been shown to inhibit both apoptosis and necrosis, and therefore greater therapeutic benefit than approaches that only inhibit one path to neuronal cell death, eg, inhibitors of NMDA receptors that only inhibit necrosis, or neurotrophic factors that only inhibit apoptosis. [See: Ferrer et al., Acta Neuropathol. (Ber) 90:504–510, 1995; Choi, Current Opinion in Neurobiology 6:667–672, 1996; Koh et al., Science 268:573–575, 1995].

ASSAY I

Displacement of $^3$H-Emopamil Binding to Guinea Pig Liver Membranes

The method of displacement of $^3$H-emopamil binding was a modification of Zech et al (1991) Eur. J. Pharm. 208:119–130.

The Guinea-pig liver membranes were prepared as follows: Male guinea pigs were sacrificed by $CO_2$ asphyxiation with dry ice. The livers were quickly excised and weighed and rinsed in membrane preparation buffer containing 10 mM Hepes, 1 mM Tris base-EDTA, 250 mM sucrose, pH 7.4. The livers were then minced homogenized in 10 times volume with a motor driven Teflon-glass homogenizer with three strokes on ice. The homogenate was centrifuged at 1000×g in a SS34 rotor for 5 minutes at 4° C. The supernatant was filtered through 4 layers of gauze and then centrifuged at 8000×g for 10 minutes 4° C. This resulting supernatant was centrifuged at 40,000×g for 15 minutes at 4° C. The resulting pellet was resuspended in assay buffer and centrifuged again at 40,000×g for 15 minutes at 4° C. This pellet was resuspended in assay buffer (2.5 fold with respect to original wet weight) and homogenized with one stroke with the Teflon-glass homogenizer. Aliquots of 1 mL were stored at −70° C.

The displacement assay was performed as follows: The reaction mixture contained: Assay buffer: 10 mM Tris-HCl, 0.1 mM phenylmethylsulfonyl fluoride (PMSF), 0.2% bovine serum albumin (BSA), pH 7.4 at 40° C.

Radioligand: 0.96 nM (−)-$^3$H-emopamil (Amersham).

Guinea pig liver membranes: 40 mg/mL original wet weight.

Compounds: 1–300 nM.

Total volume: 500 $\mu$L.

This mixture was incubated for 60 minutes at 37° C. The incubation was terminated by filtering with a Brandel Cell Harvester over Whatman GF/C filters that had been soaked for at least 120 minutes in 0.3% polyethylenamine (PEI) and washed three times with 5 mL of wash buffer containing 10 mM Tris-HCl, 10 mM $MgCl_2$, 0.2% BSA, pH 7.4 at 25° C. Specific binding was defined with 10 $\mu$M emopamil. In general compounds with an $IC_{50}$ below 1 $\mu$M in this test were of interest.

ASSAY 2

Inhibition of NMDA-induced Death of Mouse Cortical Neurons in Primary Cell Culture A glial feeder layer was prepared from post-natal day 1 or 2 mice. Cortices were dissected in a $Ca^{2+}/Mg^{2+}$-free balanced salt solution, minced, incubated in media stock (MS: GIBCO's MEM supplemented with bicarbonate, glucose, and glutamine) containing trypsin for 30 minutes at 37° C., and centrifuged at 1500 g for 5 minutes to produce a cell pellet. The pellet was re-suspended in plating media (MS supplemented with horse and fetal calf serum) and triturated with a glass pasteur pipette. Cells were plated in 24-well Falcon Primaria tissue culture dishes at a density of 0.5 hemispheres per plate. The dishes had been coated overnight with 10 mg/ml mouse laminin and 25 mg/ml poly-lysine, then washed three times with water. The glial feeder layer was maintained in a humidified atmosphere of 5% $CO_2$/95% air at 37° C. for two weeks.

Cortices prepared using similar methods from embryonic day 16 mice (from which only neurons survive in culture) were plated on the glial feeder layer at the end of two weeks at a density of 350,000 cells per well. Six days later, mixed glial/neuronal cultures were treated with 10 mM cytosine-arabinoside for 48 hours to prevent further mitosis, and then fed with fresh media containing 3 mM tamoxifen citrate. Media was exchanged with media containing fresh tamoxifen after three days. After six days of drug treatment, cultures were washed three times with a HEPES-buffered control salt solution (HCSS in mM: 120 NaCl, 5.4 KCl, 0.8 $MgCl_2$, 2.6 $CaCl_2$, 15 glucose, 20 HEPES, 10 NaOH, pH 7.4), treated with 300 $\mu$M NMDA and 10 mM glycine for five minutes in HCSS, again washed three times with HCSS, and then returned to the incubator in MS. 24 hours later, samples of cell culture media were removed from each well and tested for cell death by measuring lactate dehydrogenase (LDH) activity in the growth medium.

LDH activity was measured as follows: 50 ml of cell-culture media from each well was mixed with 200 ml 0.1 M $KH_2PO_4$ containing 30 mg NADH, in a 96-well microtitre plate. After 10 minutes at room temperature, 30 ml of 2.4 mM sodium pyruvate was added, and the absorbance of this solution at 340nm was immediately measured at 15 second intervals for approximately 6 minutes using a Molecular Devices Spectromax 250 plate-reader. NADH absorbs light at 340 nm. The rate of decline in absorption at 340 nM was fitted by linear regression to derive $V_{max}$ which is a linear function of LDH concentration. $V_{max}$ data was converted to percent neuronal death by normalizing to $V_{max}$ measurements of cell-culture media from cells not exposed to NMDA (no neuronal death) and cells exposed to 300 mM NMDA for 24 hours (complete neuronal death with glial sparing),according to the formula $(DV_{max}-CV_{max})(V_{max}-CV_{max}) \times 100$, where $DV_{max}$, $CV_{max}$, $NV_{max}$, are $V_{max}$ measurements from drug-treated cultures exposed to NMDA for 5 minutes, cultures left untreated, and cultures exposed to NMDA for 24 h, respectively. Individual experiments were repeated in quadruplicate.

ASSAY 3
Inhibition of Apoptosis in PC12 Cells Induced by NGF Withdrawal

Rat PC12 cells (ATCC Accession Number CRL-1721) were grown in RPMI0-1640 buffer containing 10% heat-inactivated Fetal Bovine Serum (FBS) and 1% L-glutamine (Gibco). Cells were plated in 100 mm Collagen I Falcon plates (Becton Dickinson)at a density of ~$1 \times 10^6$–$2 \times 10^6$ and passed every other day at 1:10 ratio (cells were trypsinized and centrifuged at 1000 rpm for 5 min. Cells were resuspended and plated at the density of 1–$2 \times 10^6$ cells). Tamoxifen was dissolved in DMSO at a concentration of 10 mM. Subsequent dilutions were done in PC12 cell growth medium containing 1% FBS.

NGF-induced differentiation and withdrawal: PC12 cells were differentiated into a neuronal phenotype in RPMI 1640 containing 1% FBS and 50 ng/ml NGF (2.5S, Cat.#N6009, Sigma). Differentiation of PC12 cells into the neuronal phenotype (neurite extension) took 9–14 days. Nerve growth factor (NGF) withdrawal was accomplished by washing the cells once with NGF-free medium. Cells were then trypsinized, centrifuged and plated onto 96-well plates at a density of ~$1 \times 10^{4/}$well. This was followed by incubation in NGF-free medium containing rabbit antibody (anti-NGF) against 2.5sNGF (Sigma catalog# N6655) at a 1:400 dilution. Drugs were added immediately after NGF withdrawal. Cells were incubated with or without drug for 3 hours and harvested by trypsinization. After 3 hr, cells were spun at 1000 RPM for 10 min, the supernatant discarded. $1 \times 10^6$ cells were used for each assay (96 well plate), Cells were harvested at various time points after the NGF withdrawal procedure to determine the time course of cell death. Apoptosis assays (Cell Death Detection ELISA) and cell necrosis assays (LDH) were conducted as described below. Compounds were used at various concentrations and the extent of apoptosis that occurred in the presence of compounds was expressed as a percentage relative to control cultures that were exposed to vehicle only. Thus, 100% was equivalent to no inhibition of apoptosis and 0% was equivalent to total inhibition of apoptosis.

ASSAY 4
Inhibition of Apoptosis in PC12 Cells Induced by b-amyloid

Rat PC12 cells were cultured as described above.

b-Amyloid (1–42), as a 1 mM aqueous stock solution (Bachem (Cat# H-1368)) was aggregated overnight at room temperature before use. Amyloid aggregation spontaneously occurs under these conditions. In initial experiments, a dose-response relationship was examined and it was determined that 100 nM b-Amyloid added to NGF differentiated PC12 cells (in the presence of NGF) for 3 hr resulted in apoptosis.

Cells were trypsinized, centrifuged at 1000 rpm for 5 min, and plated at $1 \times 10^4$ cells/well. 100 nM of aggreagted b-Amyloid was added to NGF differentiated PC12 cells. Cells were harvested by trypsinization at 3 h after the addition of b-Amyloid.

Apoptosis was measure by using Cell Death ELISA kit from Boehringer-Mannheim as described below.

ASSAY 5
Cell Death (Apoptosis) Detection ELISA for PCI 2 Cells

Cell death was measured using a Cell Death Detection ELISA (Boehringer-Mannheim Cat# 1774425) according to manufacturers instructions.The ELISA is a photometric enzyme-immunoassay which determines the amount of cytoplasmic histone-associated-DNA-fragments after induced cell death.

Cells pellets from each assay were resuspended in 200 ul lysis buffer (from kit -). The sample was placed into streptavidin-coated micotiter plate. A mixture of anti-histone-biotin and anti-DNA-peroxidase are added and incubated for an additional 2 hr. The unbound antibodies are removed by a washing step. The amount of nucleosomes is quantified by the peroxidase retained in the immunocomplex. Peroxidase was determined colorimetrically with 2,2'-Azino-di[3-ethylbenzthiazolin-sulfonat] (ABTS) as a substrate.

ASSAY 6
LDH Assay for Determining Necrosis in PC12 Cells

LDH was measured using a commercially available kit death (Boehringer-Mannheim; LDH Kit, Cat. # 1 644 793. A modification of procedure described by Koh and Choi, J. Neurosci. Methods 20:83–90, 1987). An alternative method is described in Example 2.

As stated above, differentiated PC12 cells (50 ng/ml NGF for 12 days) were used at 10,000 cells/well. To determine the LDH activity, 100 ul of the supernatant from the PC12 cells was added to reaction mixture which consists of solution I [catalyst] and Solution II [dye] and incubated for 30 min at RT. LDH activity was measure at 490 nm.

Although the pharmacological properties of the compounds of Formula I or Formula VIII vary with structural change as suspected, in general they have an affinity for the emopamil binding protein between 0.1 nM and 1 $\mu$M and in the inhibition of apoptosis in the PC12 cells assay values between 0 and 75% were measured. For example: 2,2-dimethyl-, 4-[1-[4-[2-(dimethylamino)ethoxy]phenyl]-2-phenyl-1-butenyl]phenyl Propanoic acid ester, (E)- has an $IC_{50}$ of 75 nM for the emopamil binding protein and a percentage of 41% in the PC12 assay.

The invention will now be illustrated with reference to the following non-limiting examples:

$^1$H NMR were recorded using $CDCl_3$ or $Me_2SO$-$d_6$ with $Me_4Si$ as internal reference.

Chemical shifts are in $\delta$ (ppm) and peak multiplicities are designated as follows: s, singlet; d, doublet; t, triplet; m, multiplet.

EXAMPLE 1
Phenol, 4-[2-(3-chlorophenyl)-1-[4-[2-(dimethylamino) ethoxy]phenyl]-1-butenyl]-, (Z)-prepared as described in EP 2097

EXAMPLE 2
Phenol, 4-[1-[4-[2-(dimethylamino)ethoxy]phenyl]-2-(4-ethylphenyl)-1-butenyl]-, (Z)-prepared as described in U.S. Pat. No. 4,623,660

EXAMPLE 3
Ethylamine, 2-[p-[1,2-bis(p-chlorophenyl)-1-butenyl] phenoxy]-N,N-dimethyl-, hydrochloride, (E)-prepared as described in GB 1064629

EXAMPLE 4

Ethanamine, 2-[(6-ethyl-11,12-dihydro-5-phenyldibenzo[a,e]cycloocten-2-yl)oxy]-N,N-dimethyl-prepared as described in J. Med. Chem. (1983). 26(8), 1131–7

EXAMPLE 5

Phenol, 4-[2-[2-(dimethylamino)ethoxy]-6-ethyl-11,12-dihydrodibenzo[a,e]cycloocten-5-yl]-prepared as described in J. Med. Chem. (1983), 26(8), 1131–7

EXAMPLE 6

Ethanamine, 2-[(10-ethyl-11-phenyldibenzo[b,f]thiepin-3-yl)oxy]-N,N-dimethyl-prepared as described in J. Med. Chem. (1983), 26(8), 1131–7

EXAMPLE 7

Phenol, 4-[7-[2-(dimethylamino)ethoxy]-11-ethyldibenzo[b,f]thiepin-10-yl]-prepared as described in J. Med. Chem. (1983), 26(8), 1131–7

EXAMPLE 8

Phenol, 4-[2-phenyl-1-[4-[2-(1-pyrrolidinyl)ethoxy]phenyl]-1-butenyl]-, (E)-prepared as described in U.S. Pat. No. 4,623,660

EXAMPLE 9

Ethanamine, 2-[4-[(1Z)-4-chloro-1,2-diphenyl-1-butenyl]phenoxy]-N,N-dimethyl-, (E)-prepared as described in EP 95875

EXAMPLE 10

Ethanamine, 2-[4-[1-(4-fluorophenyl)-2-phenyl-1-butenyl]phenoxy]-N,N-dimethyl-, (E)-prepared as described in Br. J. Pharmacol (1980) 71, 83–91.

EXAMPLE 11

2,2-dimethyl-, 4-[1-[4-[2-(dimethylamino)ethoxy]phenyl]-2-phenyl-1-butenyl]phenyl Propanoic acid ester, (E)-prepared as described in EP 11372

EXAMPLE 12

Benzeneacetic acid, 4-[1-[4-[2-(dimethylamino)ethoxy]phenyl]-2-phenyl-1-butenyl]phenyl ester, (E)-prepared as described in EP 11372

EXAMPLE 13

Acetic acid, methoxy-, 4-[1-[4-[2-(dimethylamino)ethoxy]phenyl]-2-phenyl-1-butenyl]phenyl ester, (E-)-prepared as described in EP 11372

EXAMPLE 14

Carbamic acid, propyl-, 4-[1-[4-[2-(dimethylamino)ethoxy]phenyl]-2-phenyl-1-butenyl]phenyl ester, (Z)-prepared as described in EP 11372

EXAMPLE 15

Phenol, 4-[1-[4-[2-(dimethylamino)ethoxy]phenyl]-2-phenyl-1-butenyl]-,phenylcarbamate(ester)(Z)-prepared as described in EP 11372

EXAMPLE 16

Benzoic acid, 4-bromo-, 4-[1-[4-[2-(dimethylamino)ethoxy]phenyl]-2-phenyl-1-butenyl]phenyl ester, (Z)-prepared as described in EP11372

EXAMPLE 17

Phenol, 4-[1-[4-[2-(dimethylamino)ethoxy]phenyl]-2-phenyl-1-butenyl]-,benzoate (ester), (E)-prepared as described in EP11372

EXAMPLE 18

Phenol, 4-[1-[4-[2-(dimethylamino)ethoxy]phenyl]-2-phenyl-1-butenyl]-, acetate (ester), (E)-prepared as described in EP 11372

EXAMPLE 19

Phenol, 4-[1-[4-[2-(dimethylamino)ethoxy]phenyl]-2-phenyl-1-butenyl]-,(Z)-4-OH Tamoxifen prepared as described in EP 2097

EXAMPLE 20

Ethanamine, 2-[4-(1,2-diphenyl-1-butenyl)phenoxy]-N,N-dimethyl-, (Z)-Tamoxifen prepared as described in U.S. Pat. No. 4,536,516

EXAMPLE 21

Piperidine, 1-[2-[4-(1,2-diphenyl-1-butenyl)phenoxy]ethyl]-, (E)-prepared as described in GB 1064629

EXAMPLE 22

Pyrrolidine, 1-[2-[p-[.beta.-ethyl-.alpha.-(p-methoxyphenyl)styryl]phenoxy]ethyl]-,(E)-prepared as described in U.S. Pat. No. 3,288,806

EXAMPLE 23

2-[p-(1,2-diphenyl-1,4-pentadienyl)phenoxy]-Triethylamine, (E)-prepared as described in BE637389

EXAMPLE 24

2,4,6-Trimethyl-benzoic acid, 4-[1-[4-[2-(dimethylamino)ethoxy]phenyl]-2-phenyl-1-butenyl] phenyl ester, (Z)-

This was prepared using 4-OH tamoxifen (Example 19) and 2,4,6-trimethylbenzoic acid following the procedure described in Example 30.

EXAMPLE 25

Ethanamine, 2-[4-[1-(2-ethylphenyl)-2-phenyl-1-butenyl]phenoxy]-N,N-dimethyl-, (Z)-4-(β-dimethylaminoethoxy)-α-ethyldesoxybenzoin (1.56 g) (prepared as in U.S. Pat. No. 4,536,516) was dissolved in 10 ml of tetrahydrofuran and added to the lithio reagent [prepared from 1-bromo-2-ethyl-benzene and butyl lithium (3.44 ml of 1.6 M) in 20 mls of tetrahydrofuran at −40° C.]. The mixture was stirred at room temperature for 2 hours. The reaction mixture was extracted with diethyl ether and purified on silica eluting with 5% triethylamine in ethylacetate.

EXAMPLE 26

Ethanamine, 2-[(10-(NN-diethylpropanamido)-11-phenyldibenzo[b,f]thiepin-3-yl)oxy]-N,N-dimethyl-7-methoxy-11-methyl-10-phenyldibenzo[b,f]thiepin was synthesized as in Acton et al [1983] J.Med.Chem 26, 1131–1137.

7-methoxy-11-methyl-10-phenyldibenzo[b,f]thiepin.(0.1 g) was dissolved in carbon tetrachloride (10 ml) and N-bromosuccinamide (0.054 g) added. The mixture was stirred and heated under reflux for 2 hours under illumination from a 60 W lamp. The mixture was cooled and the precipitated succinamide which floated to the top was filtered off. The solvent was then removed to form a white solid. The solid was recrystallised from ethyl acetate (5 ml) to give a white solid, 7-methoxy-11-bromomethyl-10-phenyldibenzo[b,f]thiepin.

Diethylmalonate (1.06 g) was added to a suspension of sodium hydride (0.48 g) in dry tetrahydrofuran (20 ml) and the suspension was stirred at room temperature under argon for 2 hours. The malonate solution filtered and the solution added to a solution of 7-methoxy-1-bromomethyl-10-phenyldibenzo[b,f]thiepin (2.7 g) in tetrahydrofuran, taking 1 hour for the addition. The mixture was stored at room temperature overnight. Sodium bromide was precipitated. Water (30 ml) was then added and the bulk of the tetrahydrofuran removed. Diethylether (50 ml) was added and a white solid was filtered off. The ether layer was taken, washed with water and a saturated sodium chloride solution, dried over magnesium sulphate and evaporated to leave an oil/solid. The oil/solid was redissolved in ether and a small amount of insoluble material filtered off. The residue was reisolated and chromatographed on silica (250 g) eluting with hexane:diethylether 100:30. Unreacted material eluted first, followed by the product, 7-methoxy-11-[(2-diethylmalon-2-yl)ethyl]-10-phenyldibenzo[b,f]thiepin.

A solution of potassium hydroxide (0.14 g) in water (10 ml) was heated to reflux and the solution stirred mechanically. 7-methoxy-11-[2-(diethylmalon-2-yl)ethyl10-phenyldibenzo[b,f]thiepin (0.244 g) dissolved in ethanol (10 ml) was added dropwise. The solution was heated to reflux and the stirred for 1.5 hours. Water (30 ml) was added and a distillate of 25 ml was taken off to remove the alcohol. A mixture of concentrated sulphuric acid (1 ml) and water (3 ml) was added and the reaction mixture was heated to reflux with stirring for 1 hour. The solution was cooled and extracted with diethylether. The product was taken into sodium bicarbonate solution and washed with diethylether. The bicarbonate solution was carefully acidified and extracted with diethylether. The diethylether extract was washed and dried to form a foam. The foam was heated on an oil bath at 165° C. for 0.5 hours. A solid, 7-methoxy-11-[(2-carboxy)ethyl]-10-phenyldibenzo[b,f]thiepin was formed on cooling. This was recrystallised from isopropanol.

7-methoxy-11-[(2-carboxy)ethyl]-10-phenyldibenzo[b,f]thiepin (The methyl ether) was demethylated as follows: Concentrated hydrochloric acid (45 ml) was added to pyridine (40 ml) and the solution was heated with stirring. The distillate being allowed to pass over until the temperature reached 210° C. and no water remained. The methyl ether (23.71 g) was heated to over 100° C. and the hot liquid pyridine hydrochloride, allowed to cool to about 50° C., poured onto it. The mixture was heated with stirring to reflux at 210° C. for 20 minutes. The reaction mixture was then poured onto ice (200 g) with stirring, whereupon the product separated as a brown gum. The mixture was extracted with diethylether (2×150 ml), the solution evaporated down and azeotroped with toluene to remove traces of pyridine. The product was filtered in diethylether solution though silica and the solution evaporated. Methylene chloride was added, whereupon the product crystallised. The product was recrystallised from diethylether with methylene chloride as above.

7-hydroxy-11-[(2-carboxy)ethyl]-10-phenyldibenzo[b,f]thiepin (1.87 g) in dry dimethylformamide (25 ml) was treated with sodium hydride (0.4 g of 75%) and stirred, first at room temperature and then at 50° C. until effervescence ceased. A solution of 1-chloro-2-NN-dimethylamino-ethane in toluene (15 ml of 1 M) was added and the mixture was heated with stirring under argon to 100° C. After 1.5 hours the mixture was allowed to cool, treated with water and extracted three times with ethyl acetate. The ethyl acetate solution was evaporated and the residue dissolved in methanol (10 ml) and 10% aqueous sodium hydroxide (5 ml) and refluxed for 20 minutes. The solvent was mostly removed and the sodium salt was dissolved in 200 ml of boiling water. Carbon dioxide was passed through the boiling solution until the pH fell to 8. This was extracted three times into ethyl acetate with a little methanol. The solution was dried and evaporated.

A solution of 2-NN-dimethylaminoethoxy-10-[(2-carboxy)ethyl]-11-phenyldibenzo[b,f]thiepin (0.74 g) in $SOCl_2$ (5 ml) was stirred for 5 minutes and the evaporated and azeotroped with dry toluene. The residue was dissolved in methylene chloride and added over approximately 2 minutes to a solution of diethylamine (1.46 g/2.07 ml) in methylene chloride (5 ml) under argon at 0° C. The reaction was allowed to warm. After 5 minutes the reaction mixture was evaporated, dissolved in ethyl acetate, filtered and evaporated. The residue was dissolved and purified on Silica using methylene chloride: methanol 100:7 as solvent. The eluante dried down and recrystallised from petroleum ether.

$^1$H NMR (90 Mhz, $CDCl_3$): 0.82 (t 6H), 1.15–1.4 (m 2H), 2.1–2.45 (m 12H), 2.63 (t 4H), 3.95 (t 2H), 6.5–7 (m 12H).

EXAMPLE 27

Ethanamine, 2-[4-(1,2-diphenyl-1-butenyl)phenoxy]-N-methyl-N-phenyl-, (Z)-

Tamoxifen (1.8 g) (Example 21) was dissolved in dry diethylether (10 ml) and methyl-magnesium-chloride (10 ml of 3.1 M) added. The diethylether was then flashed off and the residue heated at 170–200° C. for 1 hour under vacuum. On cooling the reaction mixture was quenched with diethyl ether and a saturated sodium hydrogen tartrate solution and pH adjusted to 4.5 with hydrochloric acid (1 M). This was followed by evaporation of the organic layer to yield the corresponding phenol derivative.

To the phenol derivative (3 g) a solution of potassium hydroxide pellets (0.56 g) in absolute ethanol (12 ml), containing 2 ml water was added followed by 1,2-dibromoethane (4.3 ml). The mixture was refluxed on a steam bath, with stirring for 4 hours, cooled and then filtered. The filtrate was evaporated to give a white solid mass, which was extracted with diethyl-ether. The ether extract was washed twice with 2N sodium hydroxide, water, and then dried over sodium sulphate and evaporate. This was resuspended and flash chromatographed eluting with toluene. Evaporation of the like fractions gave a clear oil which crystallised. This was recrystallised from hexane to form 1-(p-β-bromoethoxyphenyl)1,2-diphenylbut-1-ene.

A mixture of 1-(p-β-bromoethoxyphenyl) 1,2-diphenylbut-1-ene (203 mgs) and N-methylaniline (214 mg) was warmed over a steam bath for six hours. The reaction mixture was then chromatographed on silica eluting with 5% triethylamine in toluene. Similar fractions were pooled and the solvent evaporated. The resulting residue was dissolved in pet ether and left at −20° C. for several days to crystallise. The resulting crystals were re-dissolved in pet ether and recrystallised as above to give 1-(p-β-N-methyl-N-phenyl-aminoethoxyphenyl)1,2-diphenylbut-1-ene.

MS (ES+) 434 [M+H].

EXAMPLE 28

Benzoic acid, 3-amino-, 4-[1-[4-[2-(dimethylamino) ethoxy]phenyl]-2-phenyl-1-butenyl]phenyl ester, (Z)-

4-hydroxy-tamoxifen (280 mg), 3-aminobenzoic acid (120 mg), EDAC (170 mg) and DMAP (180 mg) were dissolved in methylene chloride and stirred at room temperature for 48 hours. The reaction mixture was quenched with saturated ammonium chloride (50 ml) and partitioned with methylene chloride (75 ml). The organic layer was taken and washed with saturated ammonium chloride (2×50 ml) and brine (1×50 ml). The organic layer was dried over sodium sulphate, filtered and the solvent evaporated. The residue was dissolved in methylene chloride and purified on a 4 mm silica plate using 5% methanol in methylene chloride with 0.5% ammonium hydroxide as solvent.
MS (ES+) 507 [M+H].

EXAMPLE 29

1-benzyl 4-[4-((E)-1-4-[2-(dimethylamino)ethoxy] phenyl-2-phenyl-1-butenyl)phenyl]tetrahydro-1,4 (2H)-pyridinedicarboxylate Isonipecotic acid (5 g) was dissolved in 10% sodium carbonate (100 ml) and cooled to 0° C. Then benzylformate (6.6 ml) was added dropwise and stirred at 0° C. for 30 minutes. The reaction mixture was then removed to an ice bath and stirred for 18 hours. The reaction mixture was then poured into 2 M hydrochloric acid (100 ml). Ethyl acetate (300 ml) was added and the organic layer taken and washed with hydrochloric acid (2×100 ml) and saturated sodium chloride (75 ml). The organic layer was dried over magnesium sulphate, filtered and the solvent evaporated to form CBZ-isonipecotic acid.

CBZ-isonipecotic acid (204 mg), 4-OH tamoxifen (250 mg), EDAC (148 mg) and DMAP (158 mg) were dissolved in 20 ml anhydrous methylene chloride and stirred at room temperature for 48 hours. The reaction mixture was partitioned with methylene chloride (75 ml) and 1 M sodium hydroxide (50 ml). The organic layer was 1 M sodium hydroxide (2×50 ml) and saturated sodium chloride (1×50 ml). The organic layer was dried over sodium sulphate, filtered and evaporated. The residue was purified on a 4 mm silica plate using 5% methanol in methylene chloride containing 0.5% ammonium hydroxide as solvent.
MS (ES+) 633 [M+H].

CBZ-Benzyloxycarbonyl-N-linked.

EXAMPLE 30

4-((E)-1-4-[2-(dimethylamino)ethoxy]phenyl-2-phenyl-1-butenyl)phenyl2-[(benzyloxy)carbonyl] aminoacetate 4-hydroxy-tamoxifen (250 mg) (Example 19), CBZ-glycine (162 mg), EDAC (148 mg) and DMAP (158 mg) were dissolved in 20 ml anhydrous methylene chloride. This was stiffed overnight at room temperature. Then methylene chloride (75 ml) and 1 M sodium hydroxide (50 ml) were added. The organic phase was separated off and washed with 1 M sodium hydroxide (2×50 ml) and with saturated sodium chloride (50 ml). The organic layer was dried over sodium sulphate, filtered and the solvent evaporated to yield a yellow foam. This was purified on a 4 mm silica plate using 5% methanol/methylene chloride containing 0.5% ammonium hydroxide as solvent. EDAC=1-ethyl-[3-(dimethylamino)propyl]carbodiimide.

DMAP=4-dimethyaminopyridine.
MS (ES+) 579 [M+H].
CBZ-Benzyloxycarbonyl-N-linked.
What is claimed is:

1. A compound selected from:

2,4,6-trimethyl-benzoic acid 4-{(Z)-1-[4-(2-dimethylamino-ethoxy)-phenyl]-2-phenyl-but-1-enyl}-phenyl ester;
(2-{4-[(Z)-1-(2-ethyl-phenyl)-2-phenyl-but-1-enyl]-phenoxy}-ethyl)-dimethyl-amine;
3-[3-(2-dimethylamino-ethoxy)-11-phenyl-dibenzo[b,f] thiepin-10-yl]-N,N-diethyl-propionamide;
{2-[4-((Z)-1,2-diphenyl-but-1-enyl)-phenoxy]-ethyl}-methyl-phenyl-amine;
(2-{4-[(E)-2-(4-fluoro-phenyl)-1-phenyl-but-1-enyl]-phenoxy}-ethyl)-dimethyl-amine;
3-amino-benzoic acid 4-{(Z)-1-[4-(2-dimethylamino-ethoxy)-phenyl]-2-phenyl-but-1-enyl}-phenyl ester;
piperidine-1,4-dicarboxylic acid 1-benzyl ester 4-(4-{(E)-1-[4-(2-dimethylamino-ethoxy)-phenyl]-2-phenyl-but-1-enyl}-phenyl) ester, and
benzyloxycarbonylamino-acetic acid 4-{(E)-1-[4-(2-dimethylamino-ethoxy)-phenyl]-2-phenyl-but-1-enyl}-phenyl ester;
or a pharmaceutically acceptable salt, prodrug or solvate thereof.

* * * * *